United States Patent
Sun et al.

(10) Patent No.: US 6,532,386 B2
(45) Date of Patent: *Mar. 11, 2003

(54) ELECTROTRANSORT DEVICE COMPRISING BLADES

(75) Inventors: Ying Sun; Ralph W. Oakeson, both of Somerville, NJ (US); Stephen J. Wisniewski, Doylestown, PA (US); Jonas C. T. Wang, West Windsor, NJ (US); Susan M. Niemiec, Yardley, PA (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/385,284

(22) Filed: Aug. 30, 1999

(65) Prior Publication Data

US 2002/0115957 A1 Aug. 22, 2002

Related U.S. Application Data

(60) Provisional application No. 60/098,494, filed on Aug. 31, 1998, and provisional application No. 60/129,705, filed on Apr. 16, 1999.

(51) Int. Cl.[7] .................................................. A61N 1/30
(52) U.S. Cl. ......................................................... 604/20
(58) Field of Search ........................ 604/20–22, 46–47, 604/890.1; 128/114.1, 907; 600/306, 362, 556; 424/9.8, 9.81, 449

(56) References Cited

U.S. PATENT DOCUMENTS

| | | | |
|---|---|---|---|
| 2,857,356 A | 10/1958 | Goodwin | |
| 3,315,665 A | 4/1967 | MacLeod | |
| 3,964,482 A | 6/1976 | Gerstel et al. | |
| 4,039,707 A | 8/1977 | O'Malley | |
| 4,071,028 A | 1/1978 | Perkins | |
| 4,141,359 A | 2/1979 | Jacobsen et al. | |
| 4,231,372 A | 11/1980 | Newton | |
| 4,301,794 A | 11/1981 | Tapper | |
| 4,340,047 A | 7/1982 | Tapper et al. | |
| 4,406,658 A | 9/1983 | Lattin et al. | |

(List continued on next page.)

FOREIGN PATENT DOCUMENTS

| | | |
|---|---|---|
| DE | 195 25 607 A1 | 7/1995 |
| EP | 0 429 842 A2 | 10/1990 |
| WO | WO 86/07269 | 12/1986 |
| WO | WO 92/07618 | 5/1992 |
| WO | WO 93/17754 | 9/1993 |

(List continued on next page.)

OTHER PUBLICATIONS

PCT International Search Report dated Dec. 6, 1999.
Sun, T. (1997) Skin Absorption Enhancement by Physical Means: Heat, Ultrasound, and Electricity. Transdermal and Topical Drug Delivery Systems. 327–355.

(List continued on next page.)

*Primary Examiner*—Manuel Mendez
(74) *Attorney, Agent, or Firm*—William E. McGowan

(57) ABSTRACT

The present invention relates to an apparatus for transporting a compound through a barrier membrane of a mammal comprising: (a) a vessel having a membrane contacting surface, said surface having a plurality of exposed blades and a channel adjacent to said blades; (b) a reservoir in communication with said channels for storage of said compound; and (c) an electrode in communication with said reservoir, wherein the width of said blades are tapered away from said surface.

20 Claims, 11 Drawing Sheets

U.S. PATENT DOCUMENTS

| | | |
|---|---|---|
| 4,532,924 A | 8/1985 | Auth et al. |
| 4,655,766 A | 4/1987 | Theeuwes et al. |
| 4,655,767 A | 4/1987 | Woodard et al. |
| 4,674,499 A | 6/1987 | Pao |
| 4,685,911 A | 8/1987 | Konno et al. |
| 4,722,726 A | 2/1988 | Sanderson et al. |
| 4,731,049 A | 3/1988 | Parsi |
| 4,744,788 A | 5/1988 | Mercer, Jr. |
| 4,747,819 A | 5/1988 | Phipps et al. |
| 4,752,285 A | 6/1988 | Petelenz et al. |
| 4,767,402 A | 8/1988 | Kost et al. |
| 4,790,824 A | 12/1988 | Morrow et al. |
| 4,805,616 A | 2/1989 | Pao |
| 4,898,920 A | 2/1990 | Lee et al. |
| 4,925,671 A | 5/1990 | Abber |
| 4,927,408 A | 5/1990 | Haak et al. |
| 4,979,948 A | 12/1990 | Geddes et al. |
| 4,994,267 A | 2/1991 | Sablotsky |
| 5,013,293 A | 5/1991 | Sibalis |
| 5,019,034 A | 5/1991 | Weaver et al. |
| 5,036,861 A | 8/1991 | Sembrowich et al. |
| 5,042,975 A | 8/1991 | Chien et al. |
| 5,098,430 A | 3/1992 | Fleenor |
| 5,125,928 A | 6/1992 | Parins et al. |
| 5,135,478 A | 8/1992 | Sibalis |
| 5,147,916 A | 9/1992 | Sweet |
| 5,156,591 A | 10/1992 | Gross et al. |
| 5,162,410 A | 11/1992 | Sweet |
| 5,182,938 A | 2/1993 | Merkel |
| 5,213,568 A | 5/1993 | Lattin et al. |
| 5,224,927 A | 7/1993 | Tapper |
| 5,232,702 A | 8/1993 | Pfister et al. |
| 5,250,023 A | 10/1993 | Lee et al. |
| 5,252,334 A | 10/1993 | Chiang et al. |
| 5,269,780 A | 12/1993 | Roos |
| 5,279,543 A | 1/1994 | Glikfeld et al. |
| 5,279,544 A | 1/1994 | Gross et al. |
| 5,282,799 A | 2/1994 | Rydell |
| 5,304,468 A | 4/1994 | Phillips et al. |
| 5,320,607 A | 6/1994 | Ishibashi |
| 5,362,307 A | 11/1994 | Guy et al. |
| 5,383,917 A | 1/1995 | Desai et al. |
| 5,399,163 A | 3/1995 | Peterson et al. |
| 5,438,984 A | 8/1995 | Schoendorfer |
| 5,441,490 A | 8/1995 | Svedman |
| 5,451,224 A | 9/1995 | Goble et al. |
| 5,453,360 A | 9/1995 | Yu |
| 5,514,130 A | 5/1996 | Baker |
| 5,527,288 A | 6/1996 | Gross et al. |
| 5,540,681 A | 6/1996 | Strul et al. |
| 5,533,971 A | 7/1996 | Phipps |
| 5,540,669 A | 7/1996 | Sage Jr. et al. |
| 5,542,916 A | 8/1996 | Hirsch et al. |
| 5,545,161 A | 8/1996 | Imran |
| 5,547,467 A | 8/1996 | Pliquett et al. |
| 5,563,031 A | 10/1996 | Yu |
| 5,563,042 A | 10/1996 | Phillips et al. |
| 5,571,149 A | 11/1996 | Liss et al. |
| 5,573,778 A | 11/1996 | Therriault et al. |
| 5,582,586 A | 12/1996 | Tachibana et al. |
| 5,591,124 A | 1/1997 | Phipps |
| 5,614,502 A | 3/1997 | Flotts et al. |
| 5,622,530 A | 4/1997 | Phipps |
| 5,636,632 A | 6/1997 | Bommannan et al. |
| 5,653,892 A | 8/1997 | Flotte et al. |
| 5,667,491 A | 9/1997 | Pliquett et al. |
| 5,693,052 A | 12/1997 | Weaver |
| 5,735,273 A | 4/1998 | Limol et al. |
| 5,738,107 A | 4/1998 | Martinsen et al. |
| 5,749,847 A | 5/1998 | Zewert et al. |
| 5,771,890 A | 6/1998 | Tamada |
| 5,780,050 A | 7/1998 | Srinivason et al. |
| 5,785,705 A | 7/1998 | Baker |
| 5,789,255 A | 8/1998 | Ui |
| 5,827,183 A | 10/1998 | Kurnick et al. |
| 5,843,114 A | 12/1998 | Jang |
| 5,843,692 A | 12/1998 | Phillips et al. |
| 5,853,383 A | 12/1998 | Murdock |
| 5,857,992 A | 1/1999 | Haak et al. |
| 5,865,788 A | 2/1999 | Edwards et al. |
| 5,869,326 A | 2/1999 | Hofmann |
| 5,893,885 A | 4/1999 | Webster, Jr. |
| 5,897,553 A | 4/1999 | Mulier et al. |
| 5,906,613 A | 5/1999 | Mulier et al. |
| 5,993,434 A | 11/1999 | Dev et al. |
| 6,014,584 A | 1/2000 | Hofmann et al. |
| 6,050,988 A * | 4/2000 | Zuck .................. 604/890.1 |
| 6,055,043 A | 4/2000 | Chambers |
| 6,068,650 A | 5/2000 | Hofmann et al. |
| 6,083,196 A * | 7/2000 | Trautman et al. ............ 604/46 |
| 6,096,020 A | 8/2000 | Hofmann |
| 6,117,660 A | 9/2000 | Walters et al. |
| 6,120,493 A | 9/2000 | Hofman |
| 6,148,232 A | 11/2000 | Arrahami |
| 6,181,964 B1 | 1/2001 | Hofmann |

FOREIGN PATENT DOCUMENTS

| | | |
|---|---|---|
| WO | WO 94/23777 | 10/1994 |
| WO | WO 95/30410 | 11/1995 |
| WO | WO 96/00110 | 1/1996 |
| WO | WO 96/17648 | 6/1996 |
| WO | WO 96/37256 | 11/1996 |
| WO | WO 97/12644 | 4/1997 |
| WO | WO 97/48440 | 12/1997 |
| WO | WO 97/48441 | 12/1997 |
| WO | WO 97/48442 | 12/1997 |
| WO | WO 98/11937 | 3/1998 |
| WO | WO 98/28037 | 7/1998 |
| WO | WO 98/28038 | 7/1998 |
| WO | WO 98/46124 | 10/1998 |
| WO | WO 99/22809 A1 | 5/1999 |

OTHER PUBLICATIONS

Buyuktimkin N., Buyuktimkin S. (1997) Chemical Means of Tranderdmal Drug Permeation Enhancement. Transdermal and Topical Drug Delivery Systems. 357–475.

Sun Y., Liu J.C., Xuo H. (1990) Important Parameters Affecting Iontophoretic Transdermal Delivery Of Insulin. Proceed. Intern. Symp. Control. Rel. Bioract. Mater., 17, Controlled Release Society, Inc. 202–203.

Roberts M. Lai P., Cross S., Yoshida N. (1997) Solute Structure as a Determinant of Iontophoretic Transport. Mechanisms of Transdermal Drug Delivery. 291–349.

* cited by examiner

ELECTROTRANSORT DEVICE COMPRISING BLADES

CROSS REFERENCE TO RELATED APPLICATIONS

This application claims priority from U.S. Ser. No. 60/098,494 filed Aug. 31, 1998 and U.S. Ser. No. 60/129,705 filed Apr. 16, 1999, which are both incorporated by reference.

FIELD OF THE INVENTION

The present invention relates to methods and devices for transporting molecules (e.g., active agents or interstitial fluid) across a barrier membrane (e.g., skin or mucosa).

BACKGROUND OF THE INVENTION

Transdermal and topical dosage forms have been widely prescribed for decades in the treatment of systemic diseases and local conditions such as those involved with the skin and underlying tissues. These drugs are typically "easy-to-deliver", since they easily permeate through the skin or mucosal membrane at a high potency. Permeation of the drug across the skin or mucosal membrane is a result of the chemical potential gradient across the skin or mucosal membrane. Examples of "easy-to-deliver" drugs include nitroglycerin, scopolamine, nicotine, hydrocortisone, betamethasone, benzocaine and lidocaine.

Most drugs and biological active ingredients, however, do not meet the above criteria, and therefore, are categorized as "difficult-to-deliver" drugs. Examples of "difficult-to-deliver" drugs include insulin, vasopressin, erythropoietin, interferons, and growth hormone at its releasing factors. Typically, "difficult-to-deliver" drugs have high hydrophilicity and/or high molecular weight, such as polypeptides, proteins, and DNAs.

To increase skin permeation of these drugs, various chemical and physical permeation enhancing methods have been employed. Chemical permeation enhancing agents may be applied typically to increase transdermal delivery of drugs. An extensive review of chemical penetration enhancing agents is reported in Buyuktimkin et al., "Chemical Means of Transdermal Drug Permeation Enhancement", *Transdermal and Topical Drug Delivery Systems*, Interpharm Press, Inc., 1997, pages 357–475. This method, however, is usually only effective for drugs having relatively low molecular weights (less than approximately 1000 daltons).

Electricity may also be employed to facilitate drug transport across the skin barrier by applying an electric potential gradient across the skin to facilitate drug transport. There are three types of electrically facilitated drug transport through the skin barrier, namely, iontophoresis, electro-osmosis and electroporation. In transdermal iontophoresis, an ionized drug migrates into the skin driven by an applied electric potential gradient. In electro-osmosis, a non-ionic or low-ionic drug is carried by a fluid which is driven across the skin by an applied electric potential gradient. Electroporation is the microscopic perforation of the skin barrier by extremely short pulses of high electric voltage and low current. These methods are described in Ying Sun, "Skin Absorption Enhancement by Physical Means: Heat, Ultrasound, and Electricity", *Transdermal and Topical Drug Delivery Systems*, Interpharm Press, Inc., 1997, pages 327–355.

There is a continuing need for non-invasive or minimally invasive transdermal devices for delivering active agents, especially high molecular weight drugs, such as polypeptides and proteins. Due to the high cost of high molecular weight drugs, there is a need for highly efficient minimally invasive transdermal drug delivery systems which do not cause decomposition or deactivation of the drug. Additionally, transdermal delivery devices which continually or periodically administer an active agent through skin and mucosal membrane over a long period of time and do not irritate the skin and mucosal membrane are needed.

SUMMARY OF THE INVENTION

In one aspect, the invention features an apparatus for transporting a compound across a barrier membrane of a mammal, such as the skin or mucosa membrane of a human. The compound may be an active agent, such as a drug, for therapeutic purposes, or a biologic sample (e.g., a compound with the interstitial fluid of a mammal) for diagnostic purposes. The apparatus comprises a vessel having a membrane contacting surface, a reservoir for containing the compound, and an electrode. The membrane contacting surface contains a plurality of exposed blades with a channel adjacent to the blades. The width and/or thickness of each blade is tapered away from the membrane contacting surface (e.g., the width decreases as it moves from the membrane contacting surface toward the top or tip of the blade). The reservoir is in communication with the channels and the electrode.

In one embodiment, when the membrane contacting surface contacts a barrier membrane, such as stratum corneum, the blades disrupt the barrier membrane to create pathways through the barrier membrane. The active agents in the reservoir are then forced through the pathways by electrotransport, e.g., iontophoresis. In one embodiment, liposomal formulations may be delivered by this apparatus to efficiently mediate transfection of nucleic acids into the skin cells of the basal layer of the epidermis.

Another embodiment of the invention is a transdermal electrotrasport system comprising the aforementioned apparatus, a counter electrode, and a power source, such as an electronic control unit, electrically connected to the electrode of the apparatus and the counter electrode. To deliver the active agent by electrotransport (e.g., iontophoresis, electro-osmosis, reverse electro-osmosis, or electroporation), the membrane contacting surface of the apparatus and the counter electrode are contacted with the barrier membrane of an mammal and an electrical current is applied (e.g., from the electrode, through the barrier membrane, and to the counter electrode). For example, during iontophoresis, the electrical current causes the ionized active agents, and to a lesser extent non-ionized active agents, including liposome-encapsulated active agents, in the reservoir of the apparatus to flow through the channels of the apparatus into the mammal.

In another aspect, the present invention features a method for transporting an active agent across a barrier membrane of a mammal is provided comprising penetrating the barrier membrane with a plurality of blades spaced at predetermined intervals without substantially penetrating the dermis under the barrier membrane to form pathways through the barrier membrane and applying an electrical current through the mammal to cause an active agent to flow into or out of the mammal through the pathways. Each blade is tapered toward the top of the blade.

Other features and advantages of the present invention will be apparent from the brief description of the drawings, from the detailed description of the invention, and from the claims

DETAILED DESCRIPTION OF THE INVENTION

Figure 1:
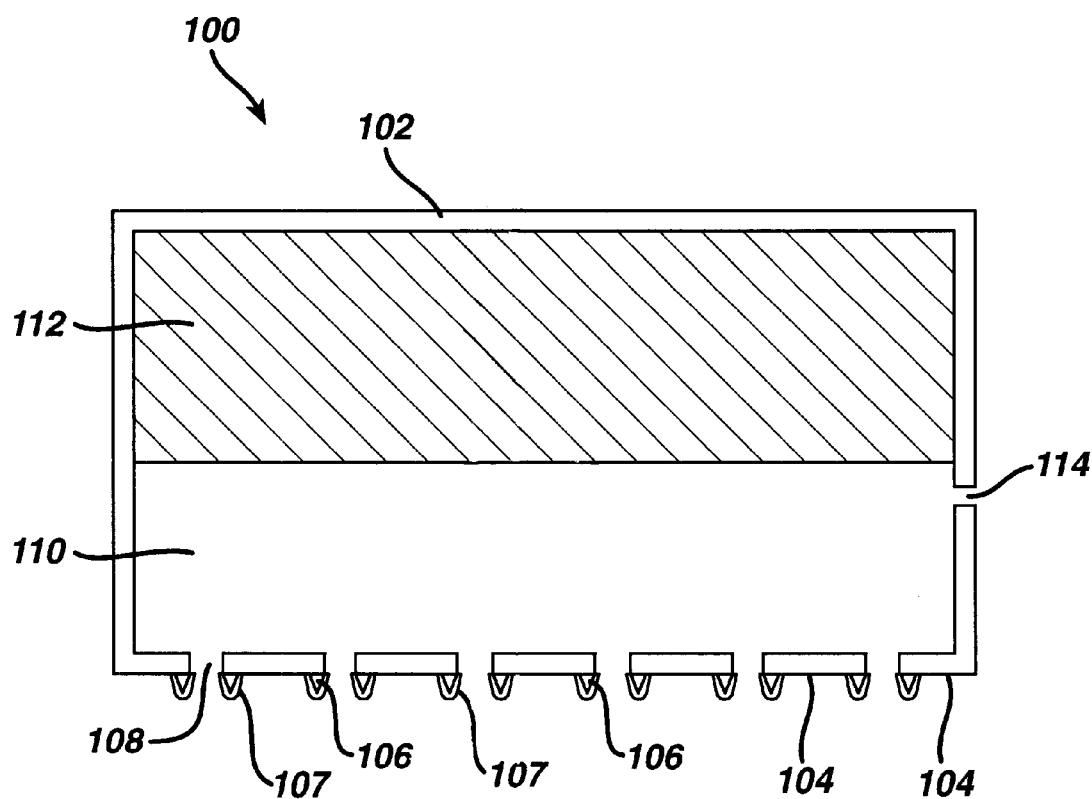
FIG. 1 is a schematic diagram of an embodiment of an electrotransport apparatus according to the present invention.
Figure 2A:
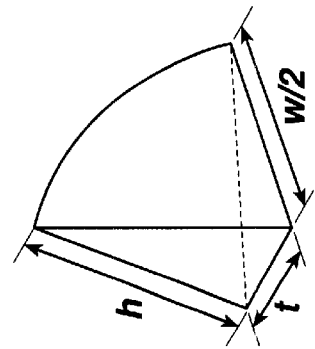
FIGS. 2A, 2B, 2C, 2D, 2E, and 2F are schematic views of shapes that can be used for the blades of a transdermal iontophoretic apparatus according to the present invention.
Figure 2B:
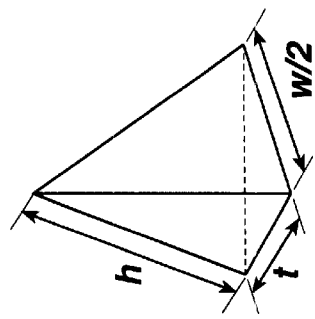
Figure 2C:
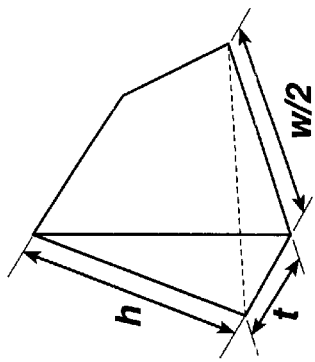
Figure 2D:
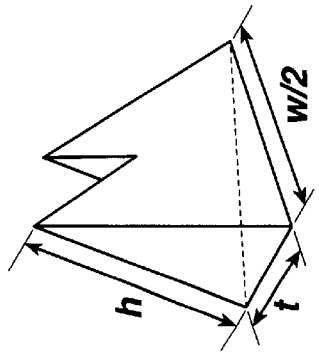
Figure 2E:
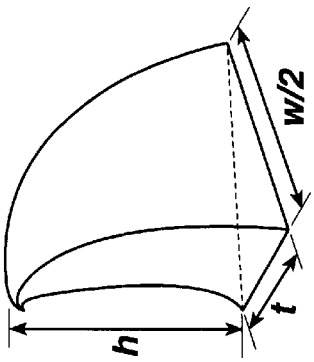
Figure 2F:
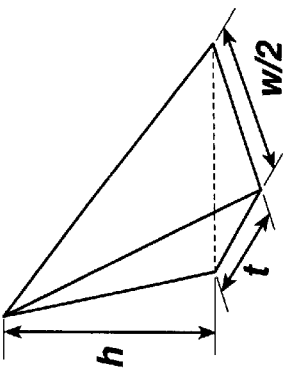

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

In one aspect, the present invention relates an apparatus for transporting an active agent across a barrier membrane (e.g., the skin and mucosal membranes such as the stratum corneum of the skin). The barrier membrane comprises at least one layer of cells (i.e., living or dead cells). This apparatus efficiently transports ionized (e.g., utilizing iontophoresis, electro-osmosis, electroporation, phonophoresis, or the force of concentration gradients or pressure) and non-ionized active agents such as liposome-encapsulated active agents or compounds in interstitial fluids (e.g., utilizing iontophoresis, electro-osmosis, electroporation, phonophoresis, or the force of concentration gradients or pressure) with minimal or no irritation across the barrier membrane. Also, this apparatus more rapidly delivers active agents than existing iontophoretic devices, without deactivating or denaturing the active agents.

Active agents which may be delivered with this apparatus include, but are not limited to, any material capable of exerting a biological effect on a human body, such as therapeutic drugs, including, but not limited to, organic compounds; drug substances; nutrients; and macromolecular compounds such as polypeptides, proteins, and nucleic acid materials comprising DNAs and antisenses. Examples of polypeptide and protein active agents include, but are not limited to, thyrotropin-releasing hormone (TRH), vasopressin, gonadotropin-releasing hormone (GnRH or LHRH), Melanotropin-stimulating hormone (MSH), calcitonin, growth hormone releasing factor (GRF), insulin, erythropoietin (EPO), interferon alpha, interferon beta, oxytocin, captopril, bradykinin, atriopeptin, cholecystokinin, endorphins, nerve growth factor, melanocyte inhibitor-I, gastrin antagonist, somatotatin, encephalins, cyclosporin and its derivatives. Suitable nutrients include, but are not limited to, vitamins, amino acids and derivatives thereof and minerals. Examples of such nutrients include vitamin B complex, thiamine, nicotinic acid, biotin, pantothenic acid, choline riboflavin, vitamin B6, vitamin B12, pyridoxine, insositol, carnitine, ascorbic acid, ascorbyl palmitate, vitamin A and its derivatives (vitamin A alcohol, vitamin A esters, vitamin A aldhyde), vitamin K, vitamin E, vitamin D, cysteine and N-acetyl cysteine, herbal extracts, and derivatives thereof. Also, other cationic and anionic active agents, such as those described in M. Roberts, et al., "Solute Structure as a Determinant of Iontophoretic Transport", *Mechanisms of Transdermal Drug Delivery*, R. O. Potts and R. H. Guy, Ed., Marcel Dekker, pages 291–349, 1997, may be delivered with this apparatus.

Referring to FIG. 1, the apparatus 100 comprises a vessel 102 having a membrane contacting surface 104. The vessel 102 may be comprised of silicone rubber; synthetic rubber; natural rubber, such as poly(isoprene), poly(butadiene-co-styrene), poly(isobutene-co-isoprene), and poly (chloroprene); and other polymeric materials commonly used for medical devices. The vessel 102 may be any shape, such as, for example, circular, oval, or rectangular. The membrane contacting surface 104 has a plurality of exposed blades 106 spaced at predetermined intervals from one another to define channels 108. Typically, the channels 108 are spaced from about 100 mm to about 10 mm from one another. The membrane contacting surface 104 may be any shape, such as, for example, circular, oval, or rectangular. In one embodiment, the membrane contacting surface 104 has an area of from about 2 to about 50 cm$^2$ (e.g., from about 10 to about 20 cm$^2$ such as about 12 cm$^2$).

The membrane contacting surface 104 and blades 106 may be comprised of hard metal materials, such as stainless steel, including, but not limited to, surgical stainless steel and high carbon steel, other alloys, and pure metals. The hard metal materials may have an electrically non-conductive outer layer. In one embodiment, the non-conductive outer layer surrounds all of the metal on the membrane contacting surface 104 such that the metal is not exposed. The non-conductive layer may be comprised of Teflon®, polyvinylidene fluoride, nylon, polysulfone, polyethersulfone, polyesters, polyethylene, and polypropylene.

Alternatively, the membrane contacting surface 104 and blades 106 may be comprised of hard non-metal materials such as polymers, including, but not limited to, copolymers and polymer blends, ceramics, crystalline materials and glassy materials. The blades 106 may be comprised of electrically non-conductive high strength materials, such as polystyrene; polycarbonate; acrylic polymers, such as polymethyl methacrylate; Teflon®; polyesters; polyurethanes; polyvinyl chlorides; fiber glass materials; biodegradable polymers, such as copolymers of polylactic acid and polyglycolic acid; ceramic materials; and inorganic glass materials.

Generally, the geometry of the blades 106 resemble the tip of a knife, namely, being thin and somewhat triangular or arc-like in shape. In one embodiment, the edges of the blades are sharp. In one embodiment, the each blade is tapered toward the top of the blade (e.g., the thickness and/ or width of the blade). The shape of the blades may be straight, curved, serrated, and/or hooked, such as, for example, as shown in FIGS. 2A–2F. In FIGS. 2A–2F, only half of the blades are being shown (i.e., only half of the face or width ("w") of the blade ("w/2") is being shown. The height of the blade is designated as "h" and the thickness of the blade is designated as "t." In one embodiment, the edges of each blade are curved (e.g., FIGS. 2A and 2E) and/or the faces of the blades are curved or slanted, e.g., toward or away from the inside of the adjacent channel) (e.g., FIGS. 2E and 2F). The blades 106 may be in groups of 2 to 10 (e.g., from 3 to 6) around a channel.

Figure 8A:
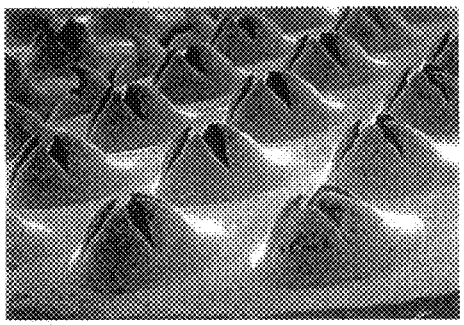
FIGS. 8A, 8B, 8C, and 8D are micrographs showing channels of the present invention surrounded by four blades.
Figure 8B:
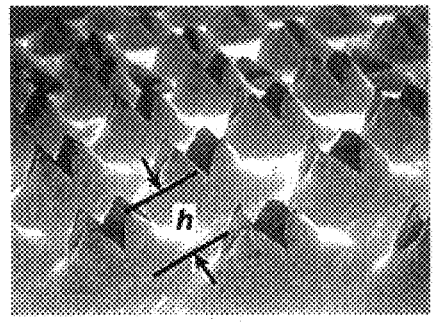
Figure 8C:
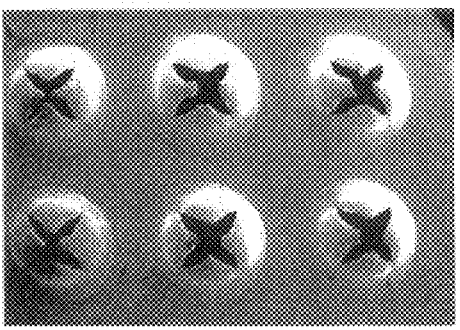
Figure 8D:
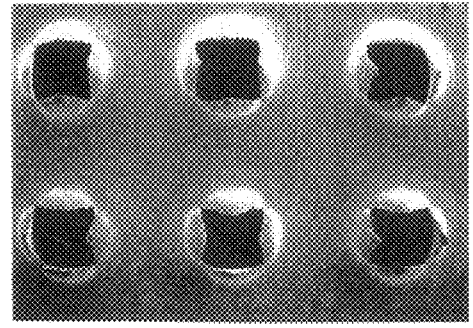
Figure 9B:
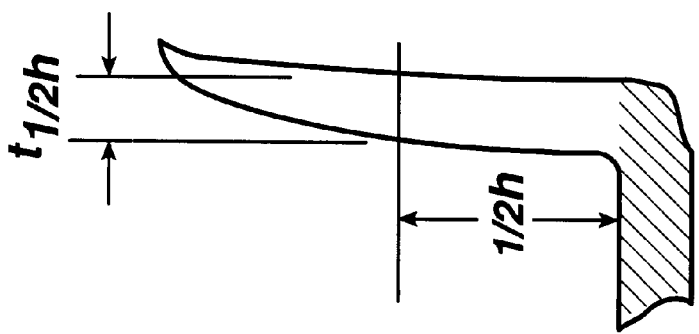
FIG. 9 is a schematic view of a shape that can be used for the blades of a transdermal iontophoretic apparatus according to the present invention.
Figure 9A:
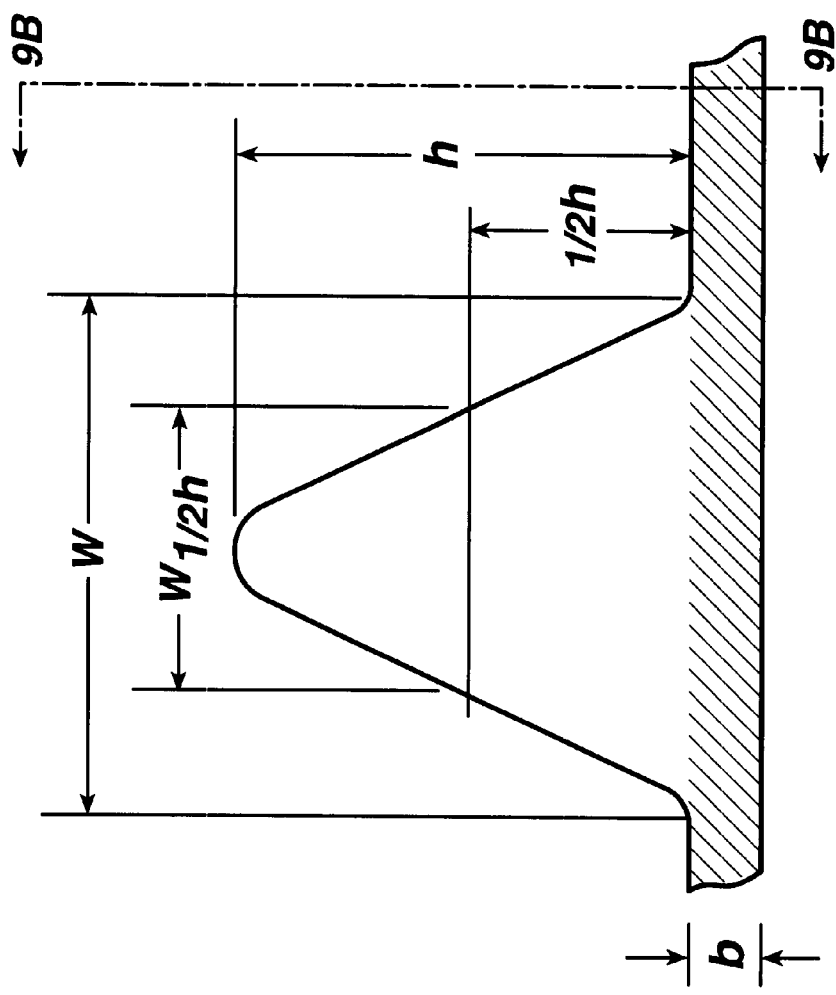

In one embodiment, the channel and its adjacent blades are formed from a single sheet of material (e.g. a thin sheet of metal such as stainless steel). See FIGS. 7, 8a, 8b, 8c, and 8d. The channels are formed by using a penetrator (e.g. a round or flat-sided awl) to pierce the sheet. As the penetrator pierces the sheet, it stretches the material until it pierces through the material, leaving a channel through the sheet and tapered, tipped blades (e.g. as depicted in FIG. 9, the width "w" of the face of the blade is greater at the bottom of the blade than at the top of the blade and the thickness "t" of the blade is greater at the bottom then at the top of the blade). The number of blades surrounding the channel will depend on the shape of the penetrator (e.g., a penetrator with four sides will create four blades). The blades may also be curved toward the channel, depending on the shape of the penetrator (e.g. if a conical or pyramidal penetrator is used) and to the extent that the penetrator pierces through the sheet. For example, a four sided penetrator can create an X-shaped channel if not substantially pushed through the channel (see FIG. 8c) or a square channel (see FIG. 8d). The manufacture of such channels and blades are discussed in PCT publication no. WO 98/11937.

Although human stratum corneum is only approximately 15 micrometers in thickness, the present inventors discovered that the height of the blades necessary to disrupt the barrier membrane was significantly greater than 15 μm. The inventors theorize that the greater height of the blades is required due to the pliability and elasticity of the stratum corneum. Therefore, the blades typically have a height greater than the thickness of the barrier membrane (e.g., greater than the thickness of the stratum corneum but less than that which will penetrate the dermis when pressed against the skin). In one embodiment, the blades 106 have a height ranging from about 100 to about 1500 μm (e.g., from about 300 to about 1,000 μm or from about 400 to about 800 μm) as measured from the base of the blade. In one embodiment, one of the blades that is adjacent to a channel is at least 25 percent greater than the other blades that are adjacent to that channel. In one embodiment, the blades, as depicted in FIG. 9, have a width-to-thickness ratio, measured at half its height ("½h") from its base (namely "W½h"/"t½h") of at least 2 (e.g., at least 5 or at least 10).

In one embodiment, when pressed against a barrier membrane such as stratum corneum or mucosa, the blades disrupt the barrier membrane only at the outmost surface without causing any substantial adverse effects to the tissue below the barrier membrane. For instance, when the blades are applied to the skin of a human being, only the stratum corneum layer and occasionally the epidermis are disrupted by the blades, leaving the dermis essentially undisturbed.

Figure 3:
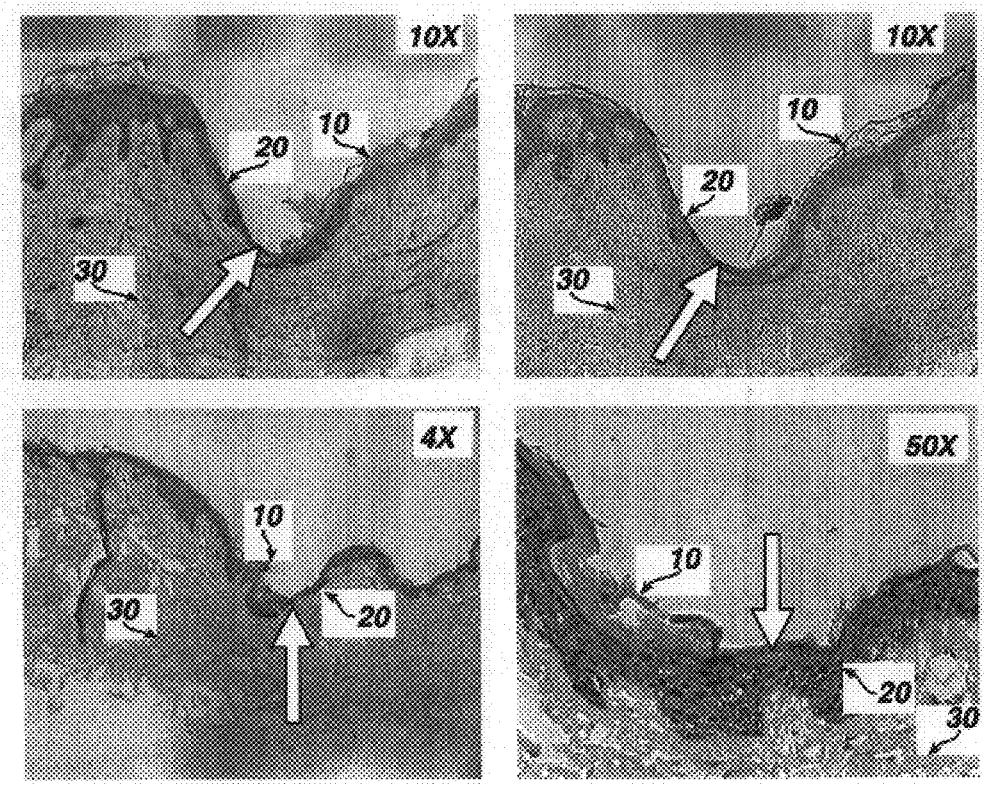
FIG. 3 are micrographs magnified at 4 times, 10 times, and 50 times showing the histological result of human cadaver skin treated with blades having a height of 800 μm.

The blades of the present invention create significantly greater openings through the barrier membrane than needles of the same height, such as those described in Lee et al., U.S. Pat. No. 5,250,023, without damaging the tissues below the barrier membrane, such as the living epidermis and/or dermis. FIG. 3 shows four microphotographs of the skin surface of a human cadaver treated with a blade having a height of 800 mm from its base. While the stratum corneum 10 has been disrupted, the epidermis 20 and dermis 30 were undisturbed.

Figure 4:
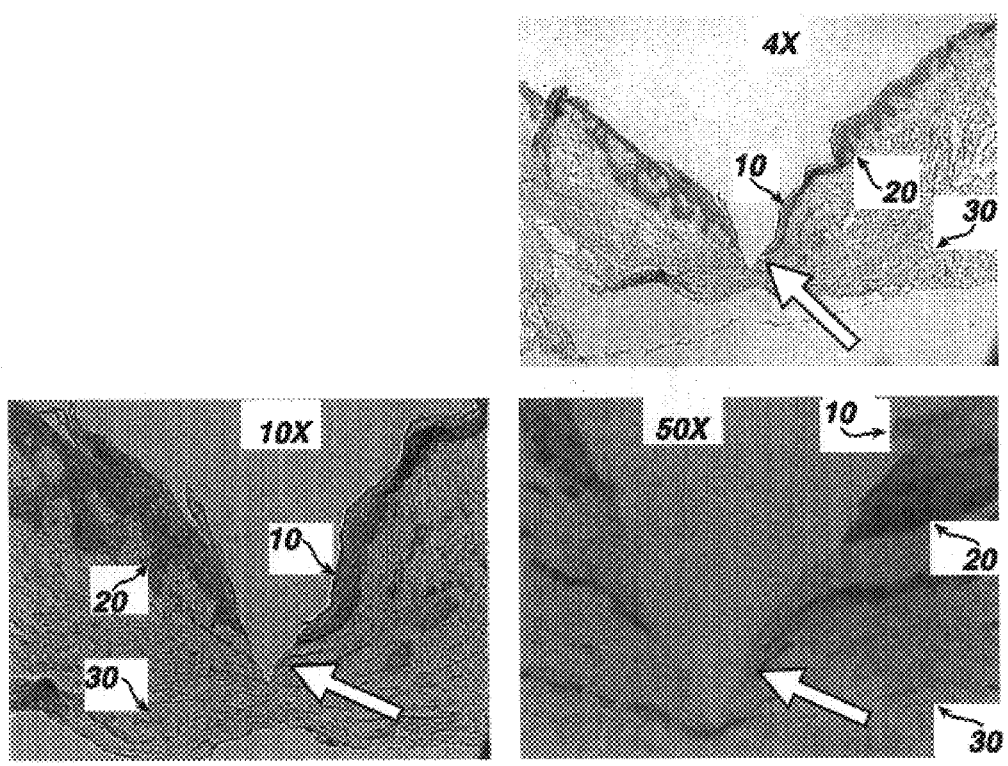
FIG. 4 are micrographs magnified at 4 times, 10 times, and 50 times showing the histological result of human cadaver skin treated with needles having a height of 800 μm.

In contrast, the pathway created with a needle usually has a very small diameter, which is further reduced by the elastic and swellable nature of the surface skin tissue. FIG. 4 shows three micrographs of the skin surface of a human cadaver treated with a needle having a height of 800 mm. As shown by FIG. 4, the human dermis 30 was injured by the needle, which usually results in pain, bleeding, and other undesirable tissue responses to wounding. Since the tissue responses to wounding are the body's natural defense system, active agents typically delivered with the assistance of needles, especially polypeptide and protein drugs, are subjected to accelerated biodegradation processes from activated enzymes and converging microphages. Also, the blades of the present invention have superior mechanical strength than needles of similar height, and therefore have a lower risk of breaking while in the skin tissues. Blades are also cheaper and simpler to produce than needles of comparable size.

The pliability and elasticity of stratum corneum can be reduced by pretreating the skin with penetration enhancing agents prior to the use of the apparatus 100. These penetration enhancing agents reduce the pliability and elasticity of stratum corneum by extracting skin lipids and moisture content from the stratum corneum. Examples of such penetration enhancing agents include, but are not limited to, lower ($C_2$–$C_5$) alcohols, such as ethanol and isopropyl alcohol; ketones, such as acetone; esters, such as ethyl acetate and butyl acetate; alkanes, such as hexane; ethers; perfluorinated hydrocarbons; surfactants; and mixtures thereof.

The stratum corneum may also be treated with penetration enhancing agents which weaken the keratin structure of the stratum corneum prior to the use of apparatus 100. These keratin-weakening penetration enhancing agents may be applied topically or by iontophoresis. Examples of these penetration enhancing agents include, but are not limited to, sulfhydryl compounds including, but not limited to, thioglycolic acid, thiolactic acid, thiosalicylic acid, and their salts of calcium, ammonium, magnesium, sodium, lithium, potassium, strontium, thioglycerol, thioethylene glycol, cysteine, acetylcysteine, homocysteine, cysteine methyl ester, cysteine ethyl ester, carbamoyl cysteine glutathione, and cysteamine; sodium sulfide; potassium sulfide; strontium sulfide; lithium sulfide; urea; salicylic acid; enzymes including, but not limited to, trypsin, chymotrypsin, thermolysin, papain and desquamin; and mixtures thereof.

The blades 106 may be moved parallel to the skin surface to increase the size of the openings on the stratum corneum. The parallel movement may be in a vibrating or oscillating motion. In one embodiment, the amplitude of the movement is less than or equal to the distance between two adjacent blades. The angle of the movement may vary, depending on the specific application (e.g., from parallel to the skin to perpendicular to the skin). The movement of the blades may also be in a circular or random motion. The movement of the blades can be driven manually or by an electric motor, which may be activated by a pressure sensor which detects when the blades are pressed against skin at a predetermined pressure. The blades may also be oscillated or vibrated parallel to the surface of the skin by a piezoelectric device at frequencies ranging from several cycles per second up to several thousand cycles per second.

In one embodiment of the apparatus 100, the blades 106 and, optionally, the membrane contacting surface 104 may have a coating 107. The coating 107 may contain the active agent to be delivered and/or the penetration enhancing agent. Moisture present in the skin or a carrier such as water from the reservoir 110 may deliver the active agent in the coating 107 to the body. Thus, when the active agent is present in the coating 107, the membrane contacting surface 104 and the coating 107 may be independently used to deliver the active agent to the mammal (e.g., the reservoir and the electrode need not be included in the device). In one embodiment, the present invention features such as device and the use of such device.

The coating 107 may further contain adjuvants to increase the mechanical strength of the coating, dissolution rate of the active agent, and stability of the active agent, and to reduce irreversible aggregation or polymerization of the active agent, especially proteins and peptides. Examples of suitable adjuvants include, but are not limited to, penetration enhancing agents described above; water-soluble polymers; mono-, di-, and polysaccharides; cyclodextrins; and antioxidants, such as ascorbic acid, ascorbic acid esters, butylhydroxyanisole, butylhydroxy-toluene, cysteine, N-acetylcysteine, sodium bisulfite, sodium metabisulfite, sodium formaldehydesulfoxylate, acetone sodium bisulfite, tocopherols, and nordihydroguaiaretic acid.

Other biological active agents may be incorporated into the coating 107 to exert biological benefits, such as to reduce irritation and/or inflammation of local tissues, to reduce unpleasant skin sensations associated with transdermal iontophoresis, to maintain the patency of the drug delivery pathways, and to provide and maintain sterility. Examples of active agents suitable for reducing irritation and/or inflammation of local tissues include, but are not limited to zinc oxide powders, histamine dihydrochloride, camphor, menthol, methyl nicotinate, methyl salicylate, turpentine oil, and corticosteroids. Examples of active agents suitable for reducing unpleasant skin sensations associated with transdermal iontophoresis include, but are not limited to, local analgesics such as lidocaine and benzocaine. Examples of active agents suitable for maintaining the patency of the drug delivery pathways include, but are not limited to, heparin, low molecular weight heparin, non-ionic surfactants, cationic surfactants and anionic surfactants. Examples of active agents suitable for providing and maintaining sterility include, but are not limited to, antimicrobial agents such as iodine, benzalkonium chloride, banzethonium chloride, triclocarban, triclosan, bacitracin zinc, neomycin, polymyxin B sulfate, and tetracyclines.

Enzyme inhibitors, such as proteolytic enzyme inhibitors and protease inhibitors, may be included in the coating 107. These inhibitors are delivered into the living skin tissue with the active agent to prevent degradation of the active agent caused by proteolytic enzymes. Proteolytic enzyme inhibitors include, but are not limited to, aprotinin, camostat mesilate, trypsin inhibitors derived from soybean or other sources, o-phenanthroline, ethylene-daminetetraaetic acid (EDTA), dilucine, sodium deoxycholate, and ovomucoid derived from duck or turkey egg whites and other sources.

In lieu of or in addition to the active agent, the coating 107 may comprise a non-conductive polymeric coating, such as Teflon®, polyvinylidene fluoride, nylon, polysulfone, polyethersulfone, polyesters, polyethylene, and polypropylene.

The coating 107 may comprise an adhesive for adhering the apparatus to the barrier membrane. The adhesive may be a polymeric, pressure sensitive and nonconductive and remains adherent even after prolonged exposure to water. Suitable adhesive materials include, but are not limited to, silicones, polyisobutylenes and derivatives thereof, acrylics, natural rubbers, and combinations thereof. Examples of adhesives include silicone adhesives and acrylic adhesives. Suitable silicone adhesives include, but are not limited to, Dow Corning® 355 available from Dow Corning of Midland, Mich.; Dow Corning® X7-2920; Dow Corning® X7-2960; GE 6574 available from General Electric Company of Waterford, N.Y.; and silicone pressure sensitive adhesives, such as those disclosed in U.S. Pat. Nos. 2,857,356; 4,039,707; 4,655,767; 4,898,920; 4,925,671; 5,147,916; 5,162,410; and 5,232,702. Suitable acrylic adhesives include, but are not limited to, vinyl acetate-acrylate multipolymers, such as Gelva® 7371, available from Monsanto Company of St. Louis, Mo.; Gelva® 7881; Gelva® 2943; I-780 medical grade adhesive available from Avery Dennison of Gainesville, Ohio; and acrylic pressure sensitive adhesives, such as those disclosed in U.S. Pat. Nos. 4,994,267; 5,186,938; 5,573,778; 5,252,334; and 5,780,050.

The adhesive affixes the apparatus to the barrier membrane (e.g., the skin) so that it is not easily separated from or moved along the skin. The adhesive also minimizes leakage of the electric current that flows through the channels 108 into the barrier membrane such as stratum corneum. Leakage of electrical current may be caused by the flow of small ions, such as hydrogen ions, hydroxyl ions, sodium ions, and the like into the intact stratum corneum, i.e., the area of the stratum corneum not disrupted by the blades 106, through the intercellular spaces between the keratin cells. A fully hydrated stratum corneum has greater intercellular spaces and, therefore, allows for greater electrolyte migration than normal stratum corneum resulting in a greater loss in electrical current. Since the active agent delivery efficiency decreases as the electrical current decreases, the leakage of electrical current reduces the active agent delivery efficiency. An electrically nonconductive or low conductive adhesive layer prevents ions flowing through the channels 108 from leaking into the stratum corneum. Instead, the ions simply flow through the pathways formed in the stratus corneum by the blades 106 without migrating to other areas of the stratum corneum. Thus, the non-conductive adhesive layer increases active agent delivery efficiency.

In addition to, or in lieu of, the adhesive in the coating 107, the apparatus 100 may be fastened to the barrier membrane with an elastic band, a band with a buckle (e.g., similar to a leather watch band), a Velcro® band, or the like.

The channels 108 may be any size large enough to permit the active agents to pass through them. Generally, the channels 108 have a diameter of from about 100 mm to about 4 mm.

A reservoir 110 is in communication with the channels 108 to either permit compounds (e.g., active agents) to exit or compounds (e.g., compounds within the interstitial fluid) to enter the reservoir 110. The reservoir 110 may be comprised of any material which is non-reactive with the active agent, including the materials which the vessel 102 may be comprised.

When used to administer a compound such as a drug, the reservoir 110 may comprises a fluid carrier which is pharmaceutically acceptable and compatible with the compound (e.g., such as water). The reservoir 100 may in addition to or in lieu of contain a suspending material for immobilizing the active agent. Examples of suspending materials include hydrophilic, highly absorbent, porous materials. Examples of suitable porous materials include, but are not limited to, cotton-based gauze; non-woven pads made of rayon or a mixture of rayon, polyester and/or other polymer fibers; polymeric foam and sponge-like materials comprised of polyurethane, polyester and/or other polymers; and cross-linked and non-cross-linked gelling materials, such as polyacrylamide, polyvinyl alcohol, gelatin, hydroxy methylcellulose, hydroxy ethylcellulose, hydroxy propylcellulose, methylcellulose, and carboxy methylcellulose. A penetration enhancing agent as described above may be incorporated into the suspending material.

The reservoir may have one or more small orifices 114 for releasing air or other gas from the reservoir in order to aid in filling the reservoir. Typically, the orifices have a diameter smaller than 100 μm. The orifices may have a valve mechanism or pressure-sensitive valve for preventing liquid in the reservoir from being released during operation.

During operation or immediately prior to operation of the apparatus 100, an active agent in a suitable solvent may be loaded into the reservoir 110. Alternatively, the reservoir 110 may be pre-loaded with a solid-state active agent. The solid-state active agent may be a powder immobilized in a porous material, such as a non-woven pad or polyurethane foam, or be in a lyophilized form, such as that obtained by freeze-drying, with or without a porous material. During operation, solvents introduced into the reservoir 110 dissolve the solid-state active agent, permitting it to come into contact with the body to which the apparatus 100 is affixed. Pharmaceutical excipients to stabilize the active agent during the lyophilization process and storage and to rapidly dissolve the active agent may be present in the reservoir 110. Examples of excipients include, but are not limited to, sodium and potassium phosphates; citric acid; tartaric acid; albumin; gelatin; and carbohydrates such as dextrose, mannitol, dextran, and cyclodextrins. In addition, the reservoir 110 may further contain penetration enhancing agents and other biological active agents as described above.

The electrode 112 may be a noble metal, such as platinum or gold, or conductive carbon. The electrode 112 may be plated onto a substrate, such as metal or conductive polymer. Suitable conductive polymers include, but are not limited to, conductive filler-embedded polymers, such as carbon-embedded silicone rubbers; carbon powder-embedded natural rubbers; silver halide powder-embedded polymers; silver halide-coated silver, such as silver chloride-coated silver, silver bromide-coated silver, and silver iodide-coated silver; and corrosive resistant alloys, such as stainless steels and titanium containing alloys. The electrode 112 may also be a combination of any of the foregoing materials.

In operation, the membrane contacting surface 104 of the apparatus 100 and a counter electrode are applied to the skin of a mammal, such as a mammal and in particular a human being. An electric potential is applied across the electrode 112 of the apparatus 100 and a counter electrode. In one embodiment, the counter electrode is identical to the apparatus 100. The current causes either a compound (e.g., an active agent) located in reservoir 110 to move through the channels 108 and into the mammal or a compound in the mammal to move through the channels 108 into the reservoir 110. The pathways through the stratum corneum created by the blades 106 decrease the electrical resistance through the stratum corneum resulting in increased electrical current through the body of the mammal. This results in greater delivery of the active agent.

The electrical current applied may be conventional direct current (DC); superimposed signals such as combining DC with conventional alternating current (AC) and the superimposed signals disclosed in U.S. Pat. No. 5,135,478; pulsed DC such as that disclosed in U.S. Pat. No. 5,042,975; and DC and pulsed DC with periodically reversed polarity as described in Y. Sun and H. Xue, Proceed. Intern. Symp. Control. Rel. Bioact. Mater., 17:202–203 (1990), and U.S. Pat. Nos. 5,224,927 and 5,013,293. In one embodiment, the current applied is direct current or pulsed direct current with periodically reversed polarity. The current density (current intensity per unit area of skin) is generally less than about 0.5 mA/cm$^2$, which is typically the pain threshold of human skin to electric current (e.g., less than 0.4 mA/cm$^2$).

The electric current or potential waveforms can be tapered at any changing points to avoid abrupt and drastic current/potential changes which may cause discomforting sensation to the mammal. For example, when iontophoresis is initiated, the current may be increased gradually to the desired intensity to minimize discomfort to the mammal.

Figure 5A:
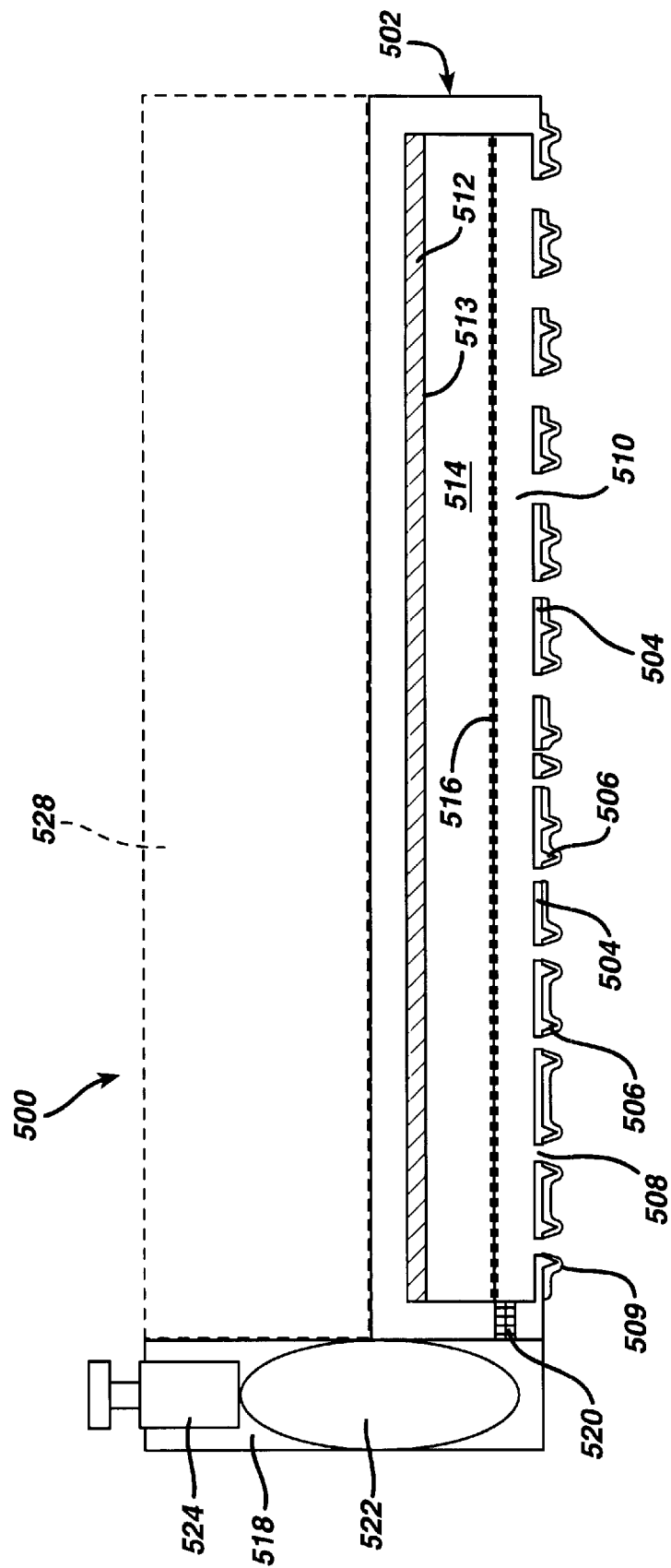
FIG. 5A is a schematic diagram of another embodiment of a transdermal iontophoretic apparatus according to the present invention.

One embodiment of the present invention is shown in FIG. 5A. The apparatus 500 comprises a vessel 502 having a membrane contacting surface 504. The membrane contacting surface 504 has a plurality of exposed blades 506 spaced at predetermined intervals from one another to define channels 508. The membrane contacting surface 504 is coated with an adhesive layer 509. A compound reservoir 510 within the vessel 502 is in communication with the channels 508 and a electrode reservoir 514.

An electrode reservoir 514 is between and in communication with a electrode 512 and the compound reservoir 501. A semipermeable membrane 516 separates the electrode reservoir 514 from the compound reservoir 501. The electrode reservoir 514 may contain an electrode medium. In order to minimize ions in the electrode medium from competing with compound/fluid ions for carrying electric charge across the skin barrier, the electrode mediums may have low or no ionic charge. Generally, the electrode medium comprises an aqueous solution containing less than about 1%, e.g., less than about 0.1% such as less than about 0.01% by weight, of electrolyte. A penetration enhancing agent as described above may be included in the electrode medium or electrode reservoir 514 to reduce the pliability and elasticity of the stratum corneum. The electrode medium may also contain from about 0.1 to about 90% by weight of other non-ionic solvents, including, but not limited to, glycerin, propylene glycol, hexylene glycol, polyethylene glycol, polypropylene glycol, and lower alcohols, such as ethanol and isopropyl alcohol.

Buffering agents to maintain the pH of the solution in the electrode reservoir 514 within a given pH range during iontophoresis may be added to the electrode medium in the electrode reservoir 514. Buffering agents include, but are not limited to, polymeric buffers, solid materials which have a buffering effect to the surrounding liquid, and the like. In one embodiment, the buffering agent is a polymeric buffer that can not pass through the semipermeable membrane 516 to the compound reservoir 501. Because of the large molecular size of the polymeric buffer, the ionized polymeric buffer has low ionic mobility and does not significantly compete with the compound/fluid ions for carrying electric charge. Therefore, the polymeric buffer does not decrease compound delivery efficiency.

The polymeric buffer may be any polymer which ionizes at a given pH by consuming hydrogen ions or hydroxyl ions and maintains the pH of the solution in the electrode reservoir 514 within a desired range. In one embodiment, the polymeric buffer has a molecular weight greater than that which can pass through the semipermeable membrane 516 (e.g., at least twice the molecular weight cut-off of the semipermeable membrane 516).

The polymeric buffer may be water soluble or water insoluble. In one embodiment, the polymeric buffer is a water insoluble polymeric buffers in the form of fine particles to maximize its surface area. Small particles of the polymeric buffer may be suspended in a gel matrix in which the active agent to be delivered is dissolved or suspended. Alternatively, the water insoluble polymeric buffer is formed into a porous polymer membrane which covers the electrode 512 and/or the internal wall of the electrode reservoir 514. The porous polymer membrane may also be used as the semipermeable membrane 516.

Polymers with acidic functional groups, i.e., anionic polymers with carboxylic functional groups such as the polymers used for enteric coatings, may be used to prevent increases in the pH of the solution in the electrode medium in the electrode reservoir 514 during cathodic iontophoresis, e.g., a negative charged active agent delivered by a negative electrode. Suitable anionic polymers include, but are not limited to, copolymers of methacrylic acid and methacrylate, such as Eudragit L available from Rohm Tech, Inc. of Malden, Mass.; Eudragit S; Eudragit RS; Eudragit RL; cellulose acetate phthalate; cellulose acetate trimellitate; and hydroxypropyl methylcellulose phthalate (HPMCP), cellulose acetate phthalate (C-A-P), and cellulose acetate trimellitate(C-A-T) available from Eastman Fine Chemicals of Kingsport, Tenn. The anionic polymer may be of a pharmaceutical grade.

An example of an anionic polymer is Eudragit S100. Below a pH of about 7, Eudragit S100 is a solid. At a pH above about 7, Eudragit S100 dissolves due to ionization of its carboxyl groups. The ionization of the carboxylic acid functional groups leads to neutralization of the excess hydroxyl ions generated by the electrochemical reaction during cathodic iontophoresis. For example, a drug formulation which is intended to be administered by iontophoresis at a pH ranging from 6.5 to 7 may utilize Eudragit S100 as a buffering agent. At a pH of 6.5 to 7, Eudragit S100 is a solid and therefore does not interfere with the active agent delivery process. As the iontophoresis process progresses, hydroxyl ions begin to build up in the solution of the electrode medium in the electrode reservoir 514 causing the pH to increase. As a result, the Eudragit S100 polymer dissolves and consumes the hydroxyl ions thereby maintaining the pH in the electrode medium within a given range.

Polymers with basic functional groups (i.e., cationic polymers such as polymers with amine groups), may be used to prevent decreases in pH during anodic iontophoresis (i.e., a positively charged active agent delivered by a positive electrode). Suitable cationic polymers include copolymers of dimethylaminoethyl methacrylate and methacrylic acid esters, such as Eudragit E available from Rohm Tech, Inc. which has a mean molecular weight of 150,000 daltons. In one embodiment, the cationic polymer is of a pharmaceutical grade. Eudragit E is solid at a pH above about 5 and dissolves at a pH below about 5. As the concentration of hydrogen ions increases due to the anodic chemical reaction, Eudragit E is ionized by absorbing the hydrogen ions, thereby maintaining the pH in the electrode medium within a given range.

The solid buffering materials may be water insoluble or have only limited aqueous solubility. Suitable solid buffering materials include, but are not limited to, calcium carbonate, aluminum oxide, aluminum hydroxide, and zinc oxide.

The electrode medium in the electrode reservoir 514 may contain other adjuvants, including, but not limited to, saccharides, polysaccharides, cyclodextrins, non-ionic surfactants, and antimicrobial agents.

In yet another embodiment, the electrode reservoir 514 is split into two or more reservoirs which may optionally be separated by semipermeable membranes.

Generally, the semipermeable membrane 516 is permeable to solvents and low molecular weight excipients, such as low molecular weight buffer species, antioxidants, chelating agents, preservatives, and tonicity adjusting ions, but not permeable to the active agent to be delivered or compound within the mammal to be analyzed. In one embodiment, only particles which have less than half (e.g., a quarter) of the molecular weight of the compound are able to permeate through the semipermeable membrane 516. For example, particles with a molecular weight less than 1,000 daltons are able to pass through the semipermeable membrane 516.

Many ionic compounds are known to participate in the electrochemical reactions at the surface 513 of the electrode 512. The electrochemical reaction of the compound often results in the degradation of the compound or deposition of the compound on the surface 513 of the electrode 512 (e.g., reducing the active agent delivery efficacy). The semipermeable membrane 516 prevents the compound from contacting the surface 513, thereby preventing degradation of the compound and deposition of the compound on the surface 513.

The semipermeable membrane 516 may be comprised of cellulose; cellulose derivatives, such as Spectra/Por® dialysis membranes available from Spectrum of Houston, Tex., regenerated cellulose, cellulose acetate, and cellulose nitrate; mixtures of cellulose with other polymeric materials, such as cellulose/polyesters and cellulose/propylene; polyethylene; polypropylene; Teflon®; polytetrafluoroethylene; polyvinylidene fluoride; nylon; polysulfone; polyethersulfone; cuprophan; polymethyl methacrylate; ethylene vinyl alcohol; polyacrylonitrile; and polymer blends of any of the foregoing.

Most protein and peptide drugs are administered by injection. These injectionable drug preparations may be introduced into the compound reservoir 510 by injection (e.g., through a septum (not shown)), pre-loading, or through a pathway 520. The injectionable drug preparations usually contain ionic excipients including preservatives such as cresol, chlorocresol, benzyl alcohol, methyl p-hydroxylbenzoate, propyl p-hydroxybenzoate, phenol, thimerosal, benzalkonium chloride, benzethonium chloride, and phenylmercuric nitrate; stabilizing agents; antioxidants such as ascorbic acid, ascorbic acid esters, butylhydroxy anisole, butylhydroxy toluene, cysteine, N-acetylcysteine, sodium bisulfite, sodium metabisulfite, sodium formaldehydesulfoxylate, sodium bisulfite, tocopherols, nordihydroguaiaretic acid; buffers; chelating agents such as ethylenediaminetetraacetic acid and its salts; buffers such as acetic acid, citric acid, phosphoric acid, glutamic acid, and salts thereof; and tonicity adjusting agents such as sodium chloride, sodium sulfate, dextrose and glycerin. These ionic excipients compete with the compound ions for carrying the electric current. Because the competing ions, i.e., the ionic excipients, are usually smaller and move faster than the compound ions, they can carry a significant amount of the electric current. Consequently, much of the electric current is diverted to moving the ionic excipients instead of the compound ions resulting, e.g., in a lower active agent delivery efficiency.

However, since the competing ions pass through the semipermeable membrane 516 into the electrode reservoir 514 while the compound does not, the concentration of competing ions in the compound reservoir 510 is reduced. Thus, more of the electrical current into the body of the mammal is carried by the compound ions instead of competing ions, resulting, e.g., in greater delivery of the active agent.

As the volume ratio of the compound reservoir 510 to the electrode reservoir 514 decreases, more of the competing ions in the compound reservoir 510 are forced into the electrode reservoir 514. Consequently, the active agent delivery efficiency increases as the volume ratio decreases. For example, at a volume ratio of 1:19, the ratio of the competing ions to active agent concentrations in the compound reservoir 510, after the competing ions have permeated through the semipermeable membrane 516 and reached equilibrium, will be 1/20'th of that ratio in the same apparatus without the semipermeable 516. It is, therefore, preferable to minimize the volume ratio of the compound reservoir 510 to the electrode reservoir 514. In one embodiment, the volume ratio is less than about 1:1 (e.g., less than about 1:10).

The apparatus may comprise one or more additional reservoirs in communication with the compound reservoir 510. A semi-permeable membrane may separate each additional reservoir from the compound reservoir 510.

An inlet 518 permits the introduction of solutions containing active agents into the compound reservoir 510 through the pathway 520. In one embodiment, the inlet 518 is adapted to receive a compound-containing capsule 522, such as those containing protein or peptide drugs which are commonly used for needle injection. The capsule 522 may be any shape but is typically cylindrical. The capsule 522 may be made of any pharmaceutically acceptable material such as glass, plastic, or metal. For a glass capsule or other breakable capsule, a plunger 524 may be pressed against the capsule 522 in the inlet 518 to crush the capsule. The solution in the capsule 522 then flows through the pathway 520 into the compound reservoir 510.

In another embodiment of the invention, the fluid in the reservoir 510 and electrode reservoir 514 may be replenished through inlet 518. The amount of fluid in these reservoirs may diminish over time due to the electrolysis of water, delivery of the fluid into the body of the mammal, leakage, and evaporation.

The pathway 520 may optionally contain a filter to prevent broken pieces of the capsule 522, such as glass debris, from entering the compound reservoir 510 and contacting the skin of the mammal. In one embodiment, the filter has a pore size of from about 0.2 $\mu$m to about 500 $\mu$m).

Figure 5B:
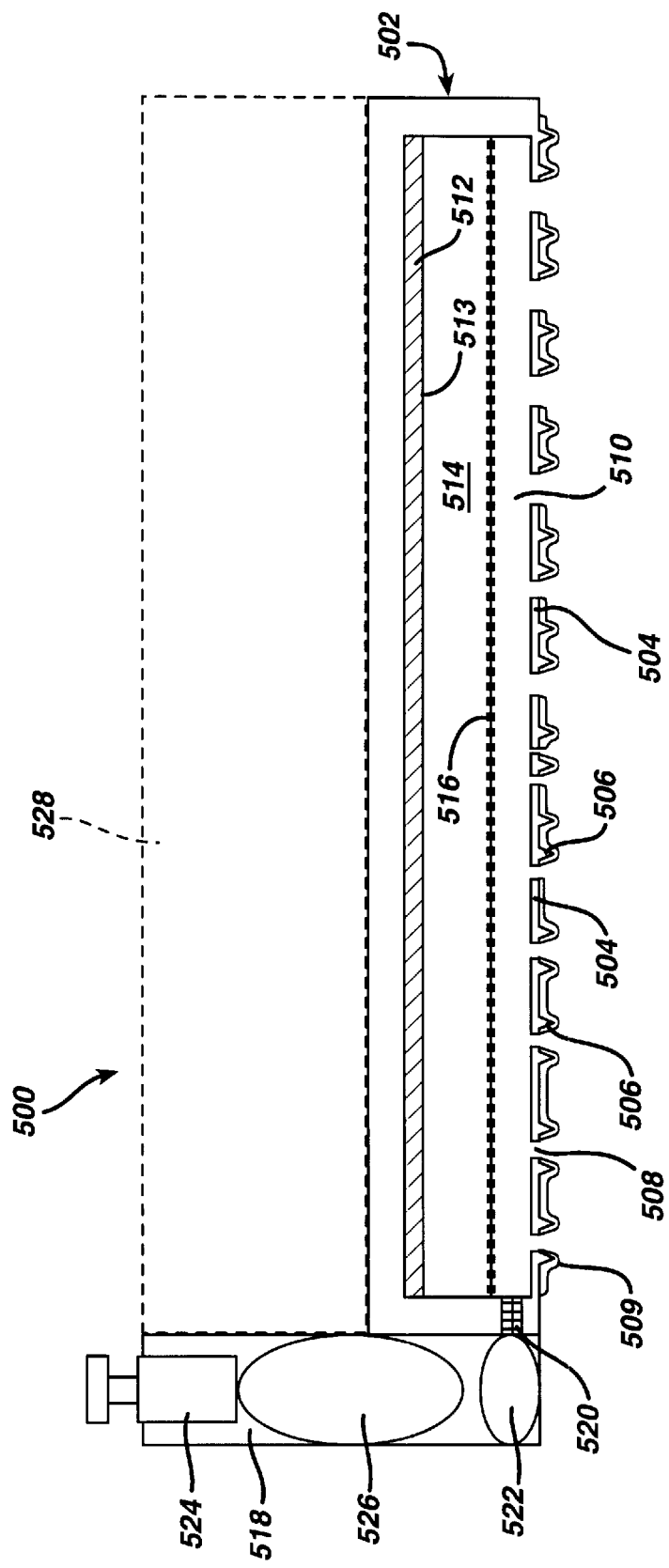
FIG. 5B is a schematic diagram of another embodiment of a transdermal iontophoretic apparatus according to the present invention.

In another embodiment shown in FIG. 5B, two capsules 522 and 526 are inserted into the inlet 518. The first capsule 522 contains a solution containing the active agent. The second capsule 526 contains a low ionic or nonionic solution, such as distilled water. The first capsule 522 is positioned closer to the pathway 520 than the second capsule such that when the plunger 524 is pressed into inlet 518, both capsules 522 and 526 are crushed causing the active agent containing solution in the first capsule 522 to enter the compound reservoir 510 followed by the low ionic solution from the second capsule 526. The low ionic solution flows through the compound reservoir 510 and the semipermeable membrane 516 into the electrode reservoir 514. As the low ionic solution flows into the electrode reservoir 514, it carriers non-active agent species, including competing ions from the compound reservoir 510. into the electrode reservoir 514. This results in increased active agent delivery efficiency.

Figure 5C:
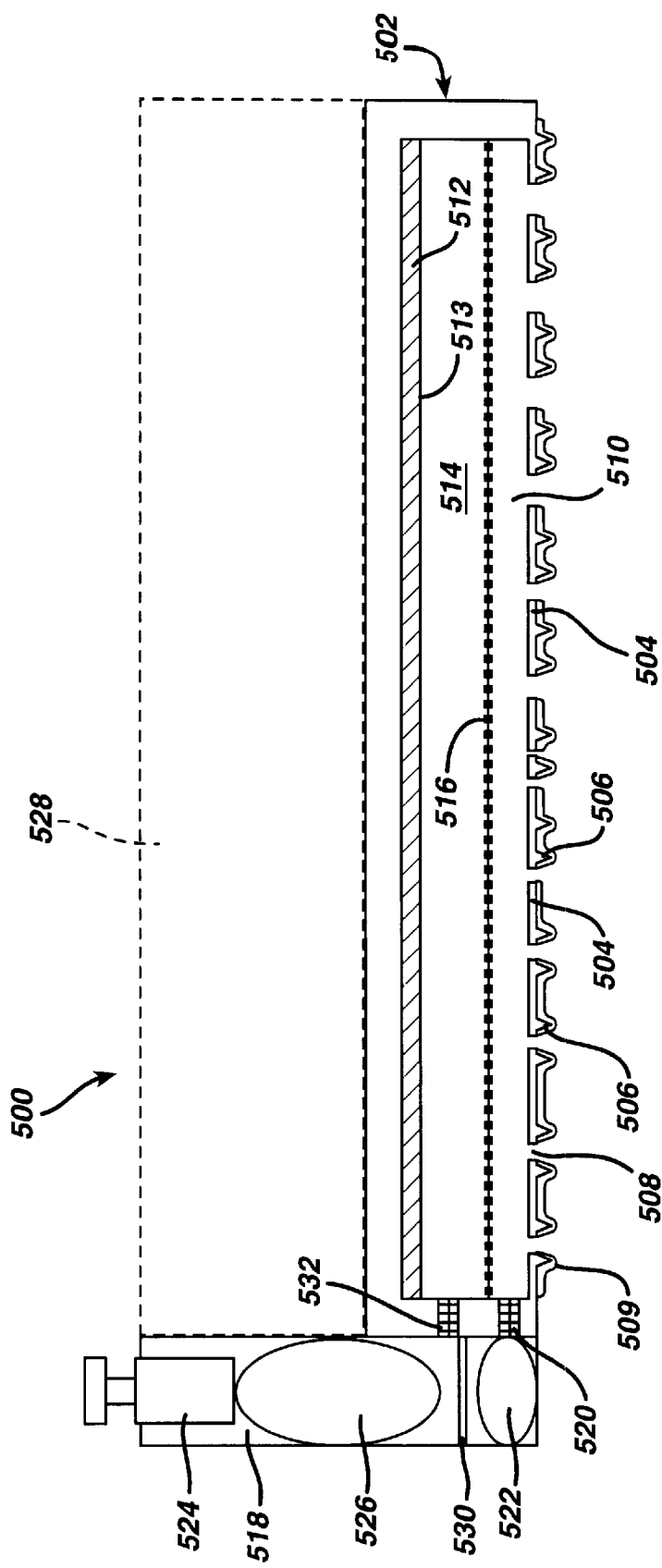
FIG. 5C is a schematic diagram of another embodiment of a transdermal iontophoretic apparatus according to the present invention.

In yet another embodiment shown in FIG. 5C, capsules 522 and 526 are separated by a diaphragm 530. The diaphragm 530 prevents the mixing of the solutions that are released when capsules 522 and 526 are crushed. The diaphragm may optionally be able to slide within inlet 518. A second pathway 532 permits fluid released from the second capsule 526 to enter the electrode reservoir 514. When the plunger 524 is pressed into inlet 518, both capsules 522 and 526 are crushed, causing the active agent containing solution from the first capsule 522 to enter the compound reservoir 510 through pathway 520 and the low ionic solution in the second capsule 526 to enter the electrode reservoir 514 through the second pathway 532.

Referring to FIG. 5A, a low ionic or nonionic solution may be injected into the compound reservoir 510 or the electrode reservoir 514 with a syringe through a self-sealing inlet (not shown) in order to reduce the number of competing ions as in the two capsule embodiment shown in FIG. 5B.

A power source and/or electronic control unit 528 is in electrical contact with the electrode 512. The electrical control unit 528 may apply an electrical current across the electrode 512 and a counter electrode (not shown) by any of the aforementioned methods.

In one embodiment, the apparatus 500 and a counter electrode identical to apparatus 500 are applied to the skin of the mammal. An electrical current is applied across the electrodes. After a predetermined period of time, the electrical polarity of the electrodes are reversed by the electronic control unit 528, causing the active agent in the counter electrode to be delivered to the mammal. The electric polarity is reversed again after another predetermined period of time has transpired. This method is continued until the iontophoresis process has been completed.

The advantages of this reversed polarity method are described in Y. Sun and H. Xue, *Proceed. Intern. Symp. Control. Rel. Bioact. Mater.,* 17:202–203 (1990). Briefly, the periodic reversal of polarity reverses the direction of the electrochemical reaction occurring at the electrical conductive material of each electrode, neutralizing the hydrogen ions and hydroxyl ions generated as a result of electrolysis of water, thereby, preventing any substantial change in pH. The length of each time interval is determined by the desired pH range to be maintained. The variability of the pH of the solution depends on many factors, such as the presence of buffers and other excipients, the electric current intensity applied, and the volume of electrolyte and active agent. In one embodiment, the pH variability between polarity reversals is about 3 pH units, about 2 pH units, or about 1 pH unit. The length of time between reversals may be preprogrammed into the electronic control unit 528. Since the contents of the apparatus 500 may be altered due to the changes in pH, the time interval between reversing polarity may be increased or decreased, gradually or in steps, in order to maintain the pH within a given pH range.

Figure 6:
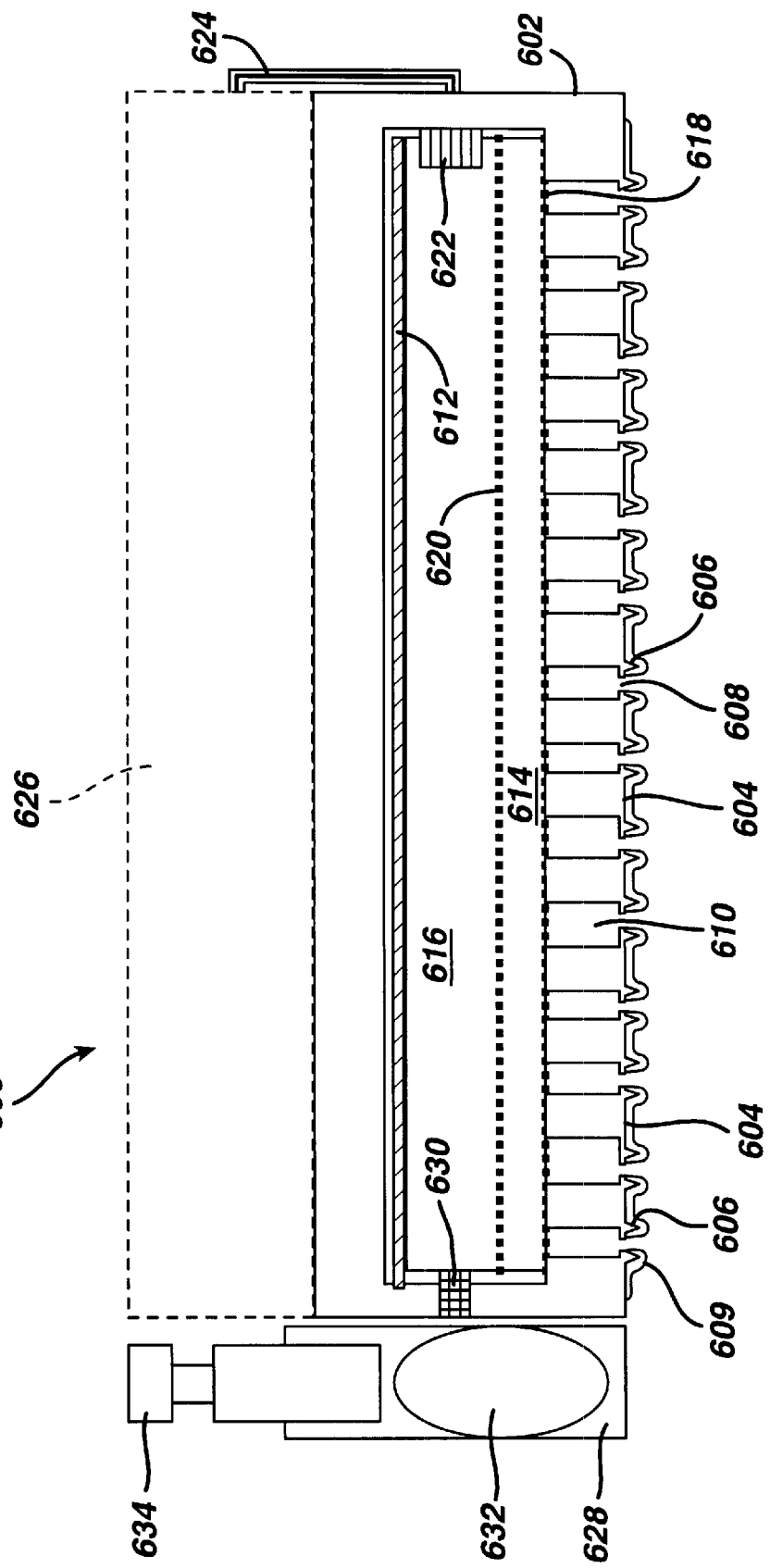
FIG. 6 is a schematic diagram of yet another embodiment of a transdermal iontophoretic apparatus according to the present invention.
Figure 7:
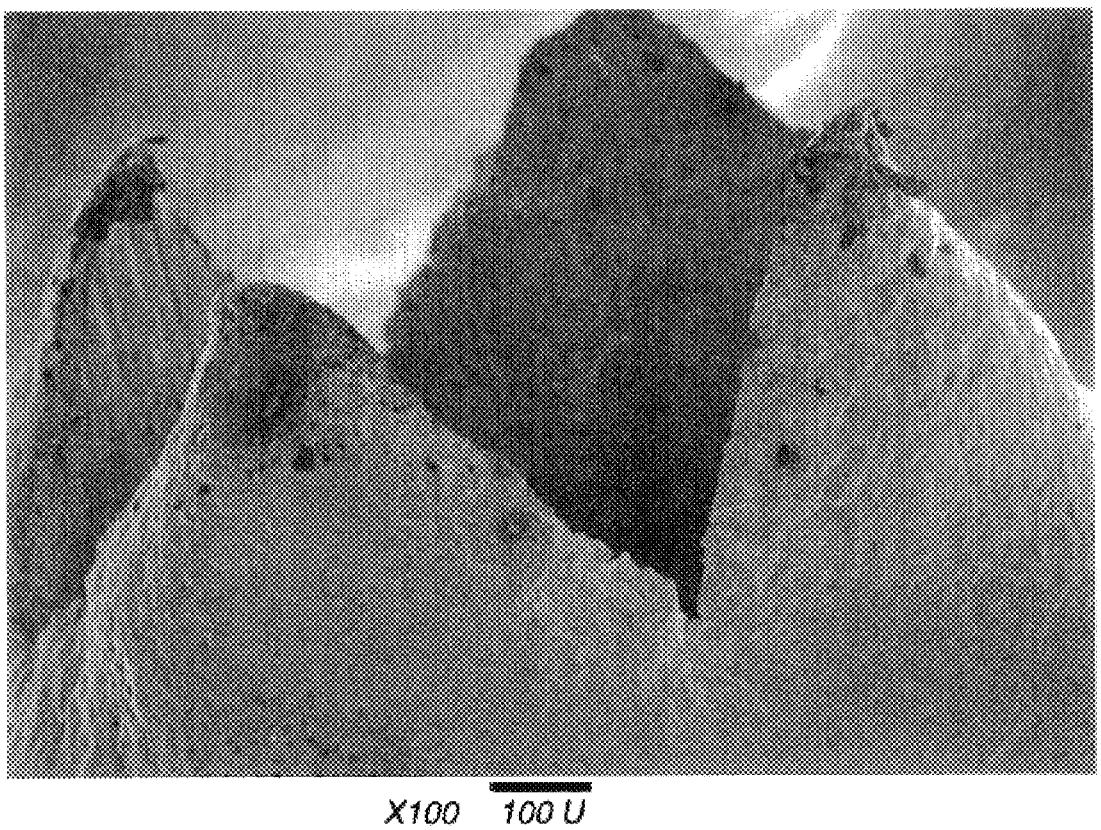
FIG. 7 is a micrograph magnified 100 times showing a channel of the present invention surrounded by three blades.

FIG. 6 illustrates another embodiment of the transdermal iontophoretic apparatus of the present invention. The apparatus 600 comprises a vessel 602 having a membrane contacting surface 604. The membrane contacting surface 604 has a plurality of exposed blades 606 spaced at predetermined intervals from one another to define channels 608. The membrane contacting surface 604 is coated with an adhesive layer 609. A plurality of compound reservoirs 610 within the vessel 602 are in communication with the channels 608 and a electrode 612. The compound reservoirs 610 are pre-loaded with the active agent in a solid state as described above, and the compound reservoirs 610 cannot communicate with one another. The separate compound reservoirs 610 prevent the active agent in each reservoir from flowing far away from the delivery pathways created by the blades 606, thus increasing the active agent delivery efficiency. The active agents may also be contained in one or more pillows, bladders, capsules, and the like. The pillows, bladders, capsules, and the like may be ruptured to release the active agent prior to installation into the apparatus 600 or by a mechanism in the apparatus 600 as would be known to one of ordinary skill in the art. The compound reservoirs 610 may be incorporated into one or more removable cartridges. Furthermore, in one embodiment, the active agent in some of the compound reservoirs 610 may be selectively released while not releasing the active agent in other compound reservoirs 610.

A electrode reservoir 614 and third reservoir 616 are between the electrode 612 and the reservoir 610. The electrode reservoir 614 is separated from the reservoir 610 by a first semipermeable membrane 618. The first semipermeable membrane 618 is permeable to solvents and low molecular excipients, but is not permeable to the active agent.

The third reservoir 616 is in communication with the electrode 612. A second semipermeable membrane 620 separates the third reservoir 616 from the electrode reservoir 614. In this embodiment, the aforementioned buffering agents are not present in the third reservoir 616. Furthermore, the second semipermeable membrane 620 prevents buffering agents from entering the third reservoir 616 from the electrode reservoir 614. This prevents the buffering agents from becoming deposited on and contaminating the electrode 612.

One or more sensors 622 in communication with the third reservoir 616 are connected through a conductive wire 624 to an electronic control unit 626. Alternatively, the sensors 622 may be in communication with the reservoir 610 and/or electrode reservoir 614 in lieu of, or in addition to, the third reservoir 616. The sensors 622 transmit detected information to the electronic control unit 626. The electronic control unit 626 controls the electrical current, including the direction of the current, and/or electrical potential through the electrode 612 and varies the electrical current and/or potential based upon the information received from the sensors 622. The electronic control unit 626 may also vary the electrical potential and current to achieve a desired delivery rate.

Suitable sensors include sensors for detecting pH; solution conductivity; halide ion concentration; compound concentration; the concentration of various acids and salts, such as sulfuric acid, nitric acid, phosphoric acid, acetic acid, and citric acid; the concentration of metal ions, such as sodium, potassium, lithium, strontium, calcium, zinc, magnesium, and aluminum; the concentration of compounds having amine functional groups or carboxylic acid functional groups; the concentration of gases, such as oxygen, hydrogen, carbon dioxide, and ammonia; color; viscosity; density; temperature; pressure; and the concentration of reactants and products of oxidation and reduction processes on electrodes. Examples of such sensors include, but are not limited to, conductivity sensors; impedance sensors; ion-selective electrodes, such as for chloride, fluoride, sulfate, silver, sodium, potassium, lithium, and ammonium ions; sensors based on amperometry, such as for oxygen and amines; sensors based on colorimentry; sensors based on spectraphotometry; and sensors based on potentiometry.

In one embodiment, the sensors 622 are pH sensors, which transmit the detected pH to the electronic control unit 626. The electronic control unit 626 reverses the polarity of the electrical current applied to the electrode 612 as previously described. The time interval between reversing polarity is increased or decreased depending on the pH variation detected and the desired pH range.

An inlet 628 permits the introduction of solutions into the third reservoir 616 through a pathway 630. The inlet 628 may be adapted to receive a capsule 632 which contains a low ionic or nonionic solution as described above. In one embodiment, a plunger 634 may be pressed against the capsule 632 in the inlet 628 to crush the capsule 632 and release the solution contained therein. When the capsule 632 is crushed, the solution enters the third reservoir 616 and flows through the second semipermeable membrane 620, electrode reservoir 614, and first permeable membrane 618 into the compound reservoirs 610. The solution then carries the active agent located in the compound reservoirs 610 through the pathways 618 into the body of the mammal to which the apparatus 600 is affixed.

In another embodiment of the invention, the fluid in the compound reservoirs 610, second reservoir 614, and/or third reservoir 616 may be replenished through inlet 628. The amount of fluid in these reservoirs may diminish over time due to the electrolysis of water, delivery of the fluid into the body of the mammal, leakage, and evaporation.

Another embodiment of the present invention is a transdermal iontophoretic system comprising the apparatus of the present invention, a counter electrode, and an electronic control unit electrically connected to the electrode of the apparatus and the counter electrode. To deliver an active agent or to obtain a compound from a mammal, the membrane contacting surface of the apparatus and the counter electrode are contacted with the barrier membrane of the mammal, such as a human, and an electrical current from the electronic control unit is applied through the electrodes. The electrical current causes the ionized active agents in the reservoir of the apparatus or compounds in the mammal to flow through the channels of the apparatus and, respectively, either into or out of the body of the mammal.

The electronic control unit may be of any shape and size, and typically will be small if the system is intended to be worn by a patient. The current supply unit provides the electric voltage/potential (e.g., it can reverse the polarity) as well as the electric current to the electrodes as needed for the electrotransport (e.g., iontophoresis, electro-osmosis, and electroporation delivery) of the active agent from the reservoir, through the orifice, and into the mammal's body though the mammal's body surface. The current supply unit may receive its energy from an external source (e.g., the electronic control unit is plugged into a standard wall outlet) or it may comprise a battery (e.g., if it is to be worn by a patient). In one embodiment, the electronic control unit and the electrodes are all contained within the same housing.

Examples of such circuits and systems are well known in the art, e.g., U.S. Pat. Nos. 4,141,359, 4,744,788, 4,747,819, 5,224,927, 4,752,285, 4,722,726, 4,731,049, 5,042,975, 5,571,149, and 5,853,383, Park, J. Neuroscience Methods, 29:85–89 (1989), Zakzewski, et al., Med. & Biol. Eng. & Comput. 34:484–88 (1996); and Jaw, et al., Med. Eng. Phys.

17:385 (1995). Examples of reverse polarity circuits are disclosed in U.S. Pat. Nos. 4,406,658 and 5,224,927.

The waveforms of electric current for electrotransport, according the present invention include, but are not limited to, conventional direct current (DC), superimposed signals such as combining DC with conventional alternating current (AC) and that disclosed in U.S. Pat. No. 5,135,478, pulsed DC such as that disclosed in U.S. Pat. No. 5,042,975, and DC and pulsed DC with periodically reversed polarity as those described by Sun, et al. (*Proceed. Intern. Symp. Control. Rel. Bioact. Mater.,* 17:202–203, 1990, and U.S. Pat. Nos. 5,224,927 and 5,013,293. The electric current or potential waveforms may be tapered at any changing points (i.e., to avoid the abrupt and drastic current/potential changes) in order to reduce the associated discomfort and undesirable skin sensation. In one embodiment, the waveform of the electric current in the present invention is DC, or pulsed DC, with periodically reversed polarity. In one embodiment, the current density (e.g., current intensity per unit are of skin) is maintained by the sensors at less than about 0.5 mA/cm$^2$ (e.g., less than about 0.4 mA/ cm$^2$).

Yet another embodiment is a method for transporting an active agent across a barrier membrane of the mammal by penetrating a barrier membrane with a plurality of blades (e.g., without or minimally penetrating the dermis) to form one or more pathways. In one embodiment, the blades are tapered toward the top of the blade as described above. In one embodiment, the blades are coated with a compound to be delivered to the mammal and/or a penetration enhancing agent and/or a membrane adhesive. In one embodiment, the active agent is then applied onto the pathways were created in the barrier membrane. In one embodiment, an electrical current is applied across the barrier membrane to cause the active agents on the barrier membrane to move through the pathways and into the body of the mammal.

In addition to the electro-transport methods (e.g., iontophoresis, electro-osmosis, and electroperforation) of enhancing material transport of the compounds into or out of the mammal discussed above, other processes well known in the art can also be used (e.g., in addition to or in lieu of electro-transport) such as ultrasound, audible sound, mechanical movement, pressure (i.e., positive pressure or negative pressure), osmotic pressure, a shock wave, heating (e.g., heating to a temperature of at least 3° C. above the temperature of the barrier membrane surface but lower than 45° C.), concentration gradients (e.g., a higher concentration of the compound on one side of the membrane), chemical enhancers, delivery of a therapeutic agent by a chemical carrier, and use of membranes adhesive (e.g., cyanacrylate polymer) to remove the membrane.

Ultrasound refers to acoustic energy with its frequency beyond the human audible range, i.e., above 20 kHz. The use of ultrasound to enhanced skin permeation of drugs is called phonophoresis or sonophoresis. The present invention uses acoustic energy of all frequencies (i.e., with frequencies above and below 20 kHz) in combination with the application of blades to enhance material transport across barrier membranes. Combination of the blades with acoustic energy can be used to enhance transdermal drug delivery, to promote the efficacy of gene therapies, and to extract biomaterials for diagnosis. The parts of the device involving the generation and propagation of acoustic energy for this purpose is similar to those currently used for drug delivery and extraction of biomaterials, e.g., as described in U.S. Pat. Nos. 4,767,402; 5,636,632; and 5,582,586.

An example of combining blade-treated barrier membranes with pressure (e.g., sudden-release pressure) is the application of a needle-free pressure injector device on the blade-treated skin for transdermal drug delivery with which the drug may be in the form of liquid or solid powder. The parts of the device involving the generation and sudden release of pressure for drug delivery purpose may be similar to those described in U.S. Pat. Nos. 4,790,824 and 5,399, 163. A vacuum, such as a Vaccutainer®, may also be used to withdraw compounds from the mammal through the blade-treated skin.

Osmotic pressure may be used to extract biomaterial out of skin or mucosa for diagnostic purpose, e.g., by placing rigid chamber containing a concentrated solution (or a gel) of solutes or polymeric materials over the skin. The chamber has an opening, which is pressed against the blade-treated skin. Osmotic pressure in the system acts to extract the biologic fluid out the skin through the disrupted barrier membrane (e.g., the stratum corneum). The positive pressure generated by osmotic pressure may also be used to increase drug delivery in a way similar to that described in the previous section (i.e., with pressure as the driving force).

A shock wave may be described as a time-dependent impulse transient characterized by an extremely short rise time with a time constant within the range of tens of nanoseconds and a magnitude of several hundred bars, with which the sudden and drastic change in medium viscosity causes a temporary permeability increase of a barrier membrane. Shock wave may be generated by a laser beam (U.S. Pat. Nos. 5,658,892 and 5,614,502), combustion, sudden release of compressed gases, or other means to enhance drug permeation through the barrier membranes in conjunction with the use of the blades. Combining the use of the blades with shock wave technology enables the use of a weaker shock wave (i.e., reducing the required energy input) to achieve drug permeation enhancement, thus reducing the potential adverse effects of shock waves, and decreasing the technical difficulties of the device fabrication.

Thermal energy in the form of heat may also be used to increase permeation of actives through blade-treated skin. The working mechanism of the heating unit in the present invention is based on electric heating, heat released from phase transition (i.e., from gas to liquid, liquid to solid, etc.), and chemical pack. The chemical pack currently available works by breaking an internal partitioning barrier to let the components mix. The subsequent mixing of the ingredients causes exothermic chemical or physicochemical reactions, thus producing heat. The device design may also be similar to that described in U.S. Pat. No. 4,685,911, which describes a self-heating transdermal patch. When the seal at the back of the patch is removed to expose the ion powder in a heating chamber to the air and water, the resulting exothermic reaction provides the thermal energy to facilitate percutaneous drug absorption.

Chemical enhancers may also be used. A chemical enhancer is defined in the present invention in a broad sense with the following functions: (a) to increase penetration of drugs and other actives through human skin and mucosa; (b) to delay or prevent the enclosure of the openings of the barrier membrane created by the blades (e.g., soluble polymers and biopolymers such as heparin of high and low molecular weight, polysaccharides such as cyclodextrins, and surface active agents such as nonionic surfactants and phosphate lipids); (c) to enhance the local blood circulation, thus facilitating the drug absorption into the blood circulation (e.g., vasodilators); (d) to enable accumulation of a permeant in the local tissues (e.g., include vasoconstrictors and the compounds capable of forming low solubility precipitates or complex with the active agent; (e) to increase drug solubility and/or chemical stability in the delivery system and around the delivery pathways (e.g., cyclodextrins, complexing agents, antioxidants, inhibitors of proteolytic enzymes and other degradative enzymes) for enhanced drug delivery; or (f) to enhance skin and mucosal tissue tolerance to the drug delivery or bio-sampling processes, e.g., reducing tissue irritation, unpleasant sensation, or any other undesirable side effects associated with the passage of the active agent through local tissues (e.g., anti-irritants, anti-inflammatory drugs, antihistamines, corticosteroids, cromolyn and its salts or derivatives, zinc salts and zinc oxide, vitamins and minerals, phytochemicals and herbal extracts). Chemical enhancers may be used prior to (e.g., as a pretreatment), during, and after the blade treatment of the barrier membrane.

A chemical carrier interacts with the active agent (e.g., drug) by encapsulation, entrapment, surface adsorption or other mechanisms to form a microscopic drug delivery system. Examples of chemical carriers are the following: (a) liposomes; (b) cyclodextrins; (c) micelles; (d) microcapsules; (e) microemulsions; (f) hydrogels; and (g) nanoparticles.

Membrane adhesives, such as cyanoacrylate polymers, may be used to strip off the membranes (e.g., the stratum corneum) to facilitate the permeation process across skin and mucosal barriers. It is well known that using adhesive materials such as Scotch tape to strip off stratum corneum could increase skin permeation of drugs. It has been reported that 100–120 tape-strippings remove stratum corneum completely. On the other hand, four strippings with cyanoacrylate adhesive have a similar effect. The working mechanism of cyanocrylate adhesives is entirely different from adhesive tapes in that cyanoacrylate liquid polymerizes upon coming in contact with the skin through reacting with the moisture and amine functional groups in the skin. Our tests indicate that striping skin more than once with cyanoacrylate glue is painful and, therefore, unlikely to be acceptable as a practical skin permeation enhancement method.

We have found that, however, when combining cyanoacrylate skin stripping with the blade treatment (e.g., applying the cyanoacrylate to the membrane contacting surface), only a single stripping was required to produce significant enhancement for iontophoretic drug delivery. The explanation for the success of this approach is that microblades facilitate the movement of liquid cyanoacrylate glue into deeper keratin layers of stratum corneum before it polymerizes, thereby enabling more effective removal of stratum corneum at the blade-treated sites. It might have resulted in wider openings on the stratum corneum, hence a higher enhancement in transdermal iontophoresis. The advantage of this approach is that only a very small fraction of the total involved skin sites was stripped off stratum corneum, as opposed to the total skin stripping method, which makes our approach much more practical as an enhancement method for transdermal drug delivery and biomaterial sampling. Thus, this method is particularly suitable for minimally invasive sampling of interstitial fluids.

While all the cyanoacrylate adhesives, such as ethylcyanoacrylate, butylcyanoacrylate, octylcyanoacrylate, etc., are useful in the present invention, the preferred cyanoacrylates are octylcyanoacrylate (Dermabond™) and n-butyl-2-cyanoacrylate (Histoacryl™), which have been used widely in many countries as a replacement of sutures for skin closure in treating lacerations.

The aforementioned permeation-enhancing methods may be used alone or in any combination. However, the combinations capable of producing a synergy in permeation enhancement and/or other benefits, such as reduced adverse effects, are preferred.

The following is a description of the use of specific apparatuses and methods of the present invention. The following examples illustrate the invention without limitation.

EXAMPLE 1

An apparatus with 800 $\mu$m blades was pressed against the epidermal surface of a piece of human cadaver skin, which was placed, on a flat elastic rubber surface with the dermis surface facing downwards. The pressure applied to the apparatus was monitored for consistency, using a pressure gauge. While the apparatus was pressed on the skin, the skin, together with the impressions created by the blades, was fixed with O.C.T freezing fixation methods (O.C.T. 4583 Compound, Tissue-Tek® available from Sakura Finetechnical Co. of Tokyo, Japan). The skin sample was then removed, sectioned, and stained for histological evaluation. The results are shown in FIG. 3. It is apparent from FIG. 3 that the stratum corneum at the application sites of the blades was clearly disrupted and that a large fraction of the stratum corneum was removed. No visible damage to the underlying epidermis or dermis is apparent, despite the use of sharp blades approximately 30 fold greater in length than the thickness of the stratum corneum and approximately 8 fold greater in length than the thickness of epidermis, which is about 100 $\mu$m thick.

Comparative Example 2

The procedure in Example 1 was repeated with an apparatus having 800 $\mu$m needles instead of 800 $\mu$m blades. The apparatus was constructed by fixing a bundle of 21 gauge injection needles on a platform, which allows only 800 $\mu$m of each needle tip to be exposed when pressed onto a cadaver skin. The results are shown in FIG. 4. The needle not only pieced through the stratum corneum, but also pierced through the underlying epidermis and cut into the dermis. Furthermore, compared to the 800 $\mu$m blades in Example 1, the area of disruption on the stratum corneum was significantly smaller.

EXAMPLE 3

The stratum corneum was physically disrupted by repeatedly scratching the skin of a pig with 400 $\mu$m blades 20 times, 10 scratchings in one direction, 10 more in a direction perpendicular to the previous direction. Two electrodes were constructed with hollow 3.5 cm by 3.5 cm by 0.5 cm polystyrene vessels each having a volume of about 5 $cm^3$. A 3 cm by 3 cm by 0.5 mm piece of stainless steel was adhered to the inside of each polystyrene vessel. The electrodes were affixed to the skin of the pig with Dow Corning 355 Medical Adhesive available from Dow Corning of Midland, Mich.

An insulin solution available as Humulin-®(500 units/ mL) from Eli Lilly and Co. of Indianapolis, Ind., was injected into the vessel with a hyperdermic needle. Iontophoresis was performed with direct current at a current intensity of 4 mA over about 12 $cm^2$ of skin. The electric polarity was manually reversed every 5 minutes for 2 hours. The blood glucose concentration and insulin serum concentration in the pig were periodically measured before, during, and after iontophoresis. The results indicated that there was a significant reduction of the blood glucose concentration (from 140 mg/dl to 30 mg/dl or about an 80% reduction) and a substantial insulin serum rise (from 25 to 590_IU/ml) in the pig.

Comparative Example 4

The procedure in Example 3 was repeated, except the stratum corneum of the pig was not disrupted with 400 μm blades and reverse polarity iontophoresis was only conducted for 30 minutes. The results indicated a lack of any reduction in blood glucose. Thus, no insulin was apparently delivered during the iontophoresis process.

EXAMPLE 5

The procedure in Example 4 was repeated, except 800 μm blades were pressed against the stratum corneum of a diabetic pig before iontophoresis was performed. The blood glucose in the pig was monitored for 9 hours.

There was approximately a 37% reduction in the blood glucose concentration in the diabetic pigs, thus correcting their hyperglycemic condition to a near normal value. Although iontophoresis was only performed for 30 minutes, the blood glucose level was maintained below 140 mg/dl for over 8 hours. It is theorized that a depot of insulin was created in the dermal tissues of the pig, which was available to maintain lower blood glucose level even after iontophoresis. This depot effect may be therapeutically beneficial since it may reduce the dosing frequency of a drug of short biological half-life with which frequent administration is often required.

EXAMPLE 6

The skin on a pig was wiped generously with 200 proof ethanol and allowed to dry to induce skin permeation enhancement. The procedure described in Example 5 was then repeated. The blood glucose concentration and insulin serum concentration in the pig were monitored for 6 hours. The transdermal iontophoresis process resulted in a serum insulin concentration of approximately 60_IU/ml after one hour and nearly a 50% reduction of blood glucose in the pig after 2 hours.

EXAMPLE 7

The procedure in Example 5 was repeated except the skin of the pig was pre-treated with Nair® lotion (containing calcium thioglycolate) available from Carter Wallace, Inc. of New York, N.Y., for 15 minutes and rinsed with warm water before the transdermal iontophoresis apparatus was applied to the skin. The calcium thioglycolate was used to reduce stratum corneum elasticity. Reverse polarity iontophoresis with insulin was performed for 120 minutes. The blood glucose concentration and insulin serum concentration in the pig were monitored for 8 hours. The results are shown in FIG. 11. The transdermal iontophoresis process resulted in a serum insulin concentration of approximately 250 IU/ml after one hour and a 30% reduction of blood glucose in the pig after 3 hours.

EXAMPLE 8

The procedure in Example 5 was repeated except that ethyl cyanoacrylate was applied to the surface of the 800 μm blades before the blades were pressed against the skin of the pig. The blades were held against the skin of the pig for 2 minutes prior to performing iontophoresis to allow the ethyl cyanoacrylate to solidify prior to removal. Reverse polarity iontophoresis with insulin was performed for 120 minutes. The blood glucose concentration in the pig was monitored for 8 hours. The quantity of insulin delivered was so large that the hyperglycemic pig having an initial blood glucose concentration of 180 mg/dl became seriously hypoglycemic with a blood glucose concentration of 25 mg/dl.

EXAMPLE 9

Gene delivery and transfection of skin after topical application of the minimally invasive blade device and liposomal/DNA delivery systems. The following methodology was used as an example.

(i) Preparation and Purification of Plasmid DNA

Expression plasmid used in these studies contained the green fluorescent protein (GFP) gene (Quantum Biotechnologies Inc., Montreal, Quebec) under the control of the cytomegalovirus (CMV) promoter (Clontech, Palo Alto, Calif.). Plasmid was prepared from DH5-alpha strain of *Escherichia coli* transformed with recombinant plasmids and grown in LB broth containing the stain of *E. coil* transformed with the recombinant plasmid and grown in LB broth containing carbenicillin (50 μg/ml). The orientation of the transgene within recombinant plasmid was confirmed by a combination of restriction endonuclease mapping and dideoxynucleotide sequencing. Plasmid DNA was purified on QUIAGEN-500 columns (Qiagen, Inc., Valencia, Calif.). Aliquots of the plasmid were then re-suspended in purified water, filtered sterilized through 0.22-μm filters (Millipore, Bedford, Mass.) and stored at −20° C. until use. The purity of all the plasmid preparations were confirmed by electrophoresis in a 1% agarose gel followed by ethidium bromide staining to detect DNA. The DNA concentration was determined at 260 and 280 nm using a spectrophotometer (Pharmacia Biotech, Inc., Piscataway, N.J).

(ii) Preparation of Liposome/Plasmid DNA Formulations

The formulations tested included aqueous DNA encoded with GFP saline and a liposomal/DNA formulation encoded with GFP in the plasmid DNA and 1 μg/pl. The liposome/DNA formulation was prepared as follows. The equal volumes of plasmid DNA (concentration 6.28μg/μl) was mixed gently with Lipofectamine™ (Life Technologies, Inc., Gaitherburg, Md.)(concentration 2 μg/ul) thus to produce a formulation that contained 3.14 μg/μl DNA and 1 μg/μl liposomes. The formulation was then incubated for 40 minutes at room temperature such that liposomes/DNA complexes can be formed before use in the experiments. The aqueous DNA was produced be added equal volumes of plasmid DNA (concentration 6.28 μg/μl) and saline to produce a formulation containing 3.14 μg/μl DNA.

(iii) In Vitro Experiments

Briefly, normal full thickness Caucasian breast skin was obtained from Sloan Kettering Memorial Hospital two hours after surgery. The subcutaneous fat was removed and the skin was punched using sterile 12-mm punches. The 12-mm explants were incubated in cell culture medium at 37° C. for 20 minutes before use. The treatment regiment included the epidermal surface being pinpricked 30 times with a 30 gauge needle, the application of a 400 or 800 μm microblade device or left untreated before application of the formulation. The untreated tissue was used as the control.

The 12-mm biopsies were placed in 12-well cell culture plates and supplemented with 750 μl of cell culture medium. The tissue was orientated in the wells such that the epidermal side of the biopsies was exposed to an air interface. The dermis was submerged in cell culture medium. 10 μl of the test formulation were applied to a 9-mm diameter area on the surface of the skin biopsies for 5 hours. The formulation was applied to the surface of a 9-mm filter and very carefully placed on top of the skin surface such that the formulation was in contact with the stratum corneum of the skin. The filter paper was be removed 5 hours later and the surface of the skin was rinsed four times with cell culture medium to remove the formulation. The experiment was terminated at 24 hours after topical application of formulation. At the end of the experiment, the skin samples were rinsed four times with medium and the tissue was embedded in fixed in 4% paraformaldahyde for two hours and then embedded in OTC medium (Miles, Inc., Elkhart, Ind.) for cryosectioning.

(iv) Detection of GFP by Immunohistochemistry

The treated tissues were embedded in OCT medium (Miles, Inc. Elkhart, Ind.) and frozen using liquid nitrogen. The frozen samples were stored at −70° C. before sectioning. Serial sections (10 μm) were obtained using a cryostat (Micron, Carl Ziess Inc., Thornwood, N.Y.) and placed on poly-L-lysine double-coated slides. The tissue sections were then processed using a Histostain-SP DAB kit (Zymed Laboratories, Inc., Burlingame, Calif.) according to the manufacture's recommendations. The sections were treated with the primary murine monoclonal GFP antibody (Clontech, Palo Alto, Calif.) for 60 minutes. After completion of the protocol, the slides were counterstained with hematoxylin, rinsed and mounted before being examined and photographed using a Nikon Optiphot microscope (Nikon, Tokyo, Japan).

(v) Detection of GFP in Mediating Gene Transfer In Vitro

This study compared the efficiency of aqueous plasmid DNA formulations, liposomal/DNA formulations and blade device, and combinations thereof to mediate transfection of DNA into cells in cultured human skin.

The DNA used in these transfections was eukaryotic expression plasmid (CMV) containing the gene for GFP. Successful transfections were detected by immunohistochemical staining with a monoclonal antibody to GFP.

TABLE 1

Groups Tested

| Group | Formulation | Total Amount of Plasmid DNA |
|---|---|---|
| Untreated Skin | None | 0 |
| Untreated Skin | Aqueous DNA | 31.4 μg |
| Untreated Skin | Liposomes/DNA | 31.4 μg |
| Pin-Pricked | Aqueous DNA | 31.4 μg |
| Pin-Pricked Blade Device | Liposome/DNA | 31.4 μg |
| 400 μm | None | 0 |
| 400 μm | Aqueous DNA | 31.4 μg |
| 400 μm | Liposomes/DNA | 31.4 μg |
| 800 μm | None | 0 |
| 800 μm | Aqueous DNA | 31.4 μg |
| 800 μm | Liposomes/DNA | 31.4 μg |

All of the formulations were prepared immediately before use and tested in triplicate for the ability to mediate transfection of plasmid DNA into skin cells.

The number of transfectant resulted from each test group was determined by visual examination of skin sections stained for GFP using immunohistochemical techniques. These results were converted to a linear scale and recorded in Table II.

The results presented in Table II indicate that, as expected, the groups where DNA was not applied did not exhibit transfection of any cells (negative controls). Unexpectedly, the groups treated with pinpricked groups did not exhibit transfected cell even though DNA was applied to the surface. Also untreated groups did not exhibit transfected cell, even though aqueous DNA and liposomal/DNA was applied. The only groups to exhibit transfection were those group where the blade devise was applied in combination with the liposomal/DNA formulation (with more transfection being present with the 800 μm blades). Even groups were the devise was applied in combination with aqueous DNA did not exhibit transfection.

TABLE II

| Group | Formulation | Relative Transfection Efficiency |
|---|---|---|
| Untreated Skin | None | 0 |
| Untreated Skin | Aqueous DNA | 0 |
| Untreated Skin | Liposomes/DNA | 0 |
| Pin-Pricked | Aqueous DNA | 0 |
| Pin-Pricked Blade Device | Liposomes/DNA | 0 |
| 400 μm | None | 0 |
| 400 μm | Aqueous DNA | 0 |
| 400 μm | Liposomes/DNA | ++ |
| 800 μm | None | 0 |
| 800 μm | Aqueous DNA | 0 |
| 800 μm | Liposomes/DNA | +++ |

These results indicate that liposomal formulation in combination with the blade device can effectively disable the barrier function of the stratum corneum and delivery plasmid DNA into cells and the gene product can be produced.

It is understood that while the invention has been described in conjunction with the detailed description thereof, that the foregoing description is intended to illustrated and not limit the scope of the invention, which is defined by the scope of the appended claims. Other aspects, advantages, and modifications are within the claims.

What is claimed is:

1. An apparatus for transporting a compound through a barrier membrane of a mammal comprising:
    (a) a vessel having a membrane contacting surface, said surface having a plurality of exposed blades and a channel adjacent to said blades;
    (b) a reservoir in communication with said channels for storage of said compound; and
    (c) an electrode in communication with said reservoir, wherein the width and the thickness of said blades are tapered away from said surface.

2. An apparatus as defined in claim 1, wherein said channel is adjacent to at least three blades.

3. An apparatus as defined in claim 2, wherein said surface comprises a plurality of channels, where said channels are adjacent to at least three blades.

4. An apparatus as defined in claim 3, wherein the height of one of said blades adjacent to said channels is at least 25 percent greater than the other blades.

5. An apparatus as defined in claim 3, wherein at least one side of the face of said blades are curved.

6. An apparatus as defined in claim 3, wherein said channels are spaced from about 100 mm to 10 mm from one another.

7. An apparatus as defined in claim 3, wherein said blades comprise one or more non-electrical conductive materials.

8. An apparatus as defined in claim 3, wherein the edges of said blade are curved.

9. An apparatus as defined in claim 3, wherein said blades have a height of from about 100 to about 1,500 mm.

10. An apparatus as defined in claim 3, wherein said blades have a width to thickness ratio measured at half the height of said blades of at least 2.

11. An apparatus as defined in claim 1, wherein said reservoir comprises:
    an electrode reservoir in communication with said electrode;

a compound reservoir in communication with said channels; and a semipermeable membrane in communication with said electrode reservoir and said compound reservoir.

12. An apparatus as defined in claim 11, wherein said semipermeable membrane only permeates molecules having a molecular weight less than the molecular weight of said compound.

13. An apparatus as defined in claim 11, wherein the volume ratio of said compound reservoir to said electrode reservoir is less than about 1.

14. An apparatus as defined in claim 1, further comprising an electronic control unit electrically connected to said electrode, said electronic control unit for controlling the electrical current through said electrode.

15. An apparatus as defined in claim 14, further comprising at least one sensor, said sensor transmitting detected information to said electronic control unit, said electronic control unit varying the electrical current through said electrode dependent on the information received from said sensor.

16. An apparatus as defined in claim 15, wherein said sensor is selected from the group consisting of a pH sensor, conductivity sensor, ion-selective electrode, sensor based on amperometry, and sensor based on potentiometry.

17. A transdermal iontophoretic system comprising:

(a) a first electrode comprising (1) a vessel having a membrane contacting surface, said membrane contacting surface having a plurality of exposed blades and channels adjacent said blades wherein the width and the thickness of said blades are tapered away from said surface;

(2) a reservoir in communication with said channels; and (3) an electrode in communication with said reservoir;

(b) a counter electrode; and (c) an electronic control unit, wherein said electronic control unit is electrically connected to said electrode and said counter electrode, and said electronic control unit controls the electrical current through said electrode.

18. A method for transporting a compound across a barrier membrane of a mammal comprising:

(a) penetrating said barrier membrane with a plurality of blades spaced at predetermined intervals to form pathways through said barrier membrane; and (b) applying an electrical current through said mammal to cause a compound to cross said barrier membrane through said pathways, wherein the width and the thickness of said blades are tapered away from said surface.

19. A method of claim 18, wherein said method further comprises administering to said barrier membrane a penetration enhancing agent.

20. An apparatus as defined in claim 1, wherein said apparatus further comprises a counter electrode and an electronic control unit, wherein said electronic control unit is electrically connected to said electrode and said counter electrode, and said electronic control unit controls the electrical current through said electrode.

* * * * *